(12) United States Patent
Chen et al.

(10) Patent No.: US 10,281,464 B2
(45) Date of Patent: May 7, 2019

(54) REAL-TIME DETECTION OF WATER CONTAMINANTS

(71) Applicant: UWM Research Foundation, Inc., Milwaukee, WI (US)

(72) Inventors: Junhong Chen, Whitefish Bay, WI (US); Jingbo Chang, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 10 days.

(21) Appl. No.: 15/500,943

(22) PCT Filed: Aug. 3, 2015

(86) PCT No.: PCT/US2015/043449
§ 371 (c)(1),
(2) Date: Feb. 1, 2017

(87) PCT Pub. No.: WO2016/019381
PCT Pub. Date: Feb. 4, 2016

(65) Prior Publication Data
US 2017/0234861 A1    Aug. 17, 2017

Related U.S. Application Data

(60) Provisional application No. 62/032,280, filed on Aug. 1, 2014.

(51) Int. Cl.
*G01N 33/543* (2006.01)
*G01N 27/414* (2006.01)
(Continued)

(52) U.S. Cl.
CPC ........... *G01N 33/5438* (2013.01); *C12Q 1/10* (2013.01); *C12Q 1/689* (2013.01); *G01N 27/4145* (2013.01); *G01N 27/4146* (2013.01); *G01N 33/1826* (2013.01); *G01N 33/1886* (2013.01); *G01N 33/54346* (2013.01); *G01N 33/56916* (2013.01); *G01N 2333/245* (2013.01)

(58) Field of Classification Search
None
See application file for complete search history.

(56) References Cited

U.S. PATENT DOCUMENTS 5,521,289 A    5/1996  Hainfeld et al.
6,258,254 B1   7/2001  Miyamoto et al.
(Continued)

FOREIGN PATENT DOCUMENTS

| CN | 101941696 A | 1/2011 |
| CN | 103531424 A | 1/2014 |
| CN | 203732494 U | 7/2014 |

OTHER PUBLICATIONS

Kang et al "MEcahanisnn of the effects of low temperature Al2O3 passivaiton on graphene filed effect transistors" Carbon, Oct. 26, 2012, 53: 182-187. (Year: 2012).*
(Continued)

*Primary Examiner* — Betty J Forman
(74) *Attorney, Agent, or Firm* — Michael Best & Friedrich LLP

(57) ABSTRACT

Provided herein is a field-effect transistor based sensor for real-time detection of water contaminants and methods of use thereof.

25 Claims, 19 Drawing Sheets

(51) Int. Cl.
*C12Q 1/10* (2006.01)
*C12Q 1/689* (2018.01)
*G01N 33/18* (2006.01)
*G01N 33/569* (2006.01)

(56) References Cited

U.S. PATENT DOCUMENTS

| | | | |
|---|---|---|---|
| 7,208,587 | B2 | 4/2007 | Mirkin et al. |
| 7,235,170 | B2 | 6/2007 | Watanabe et al. |
| 7,465,953 | B1 | 12/2008 | Koh et al. |
| 8,476,510 | B2 | 7/2013 | Swager et al. |
| 9,676,621 | B2 * | 6/2017 | Chen .................. B82Y 15/00 |
| 2006/0205013 | A1 | 9/2006 | Shim et al. |
| 2007/0048796 | A1 | 3/2007 | Kubo et al. |
| 2008/0009002 | A1 | 1/2008 | Gruner et al. |
| 2009/0057650 | A1 | 3/2009 | Lieber et al. |
| 2010/0025660 | A1 | 2/2010 | Jain et al. |
| 2010/0053624 | A1 | 3/2010 | Yoo et al. |
| 2010/0178464 | A1 | 7/2010 | Choi et al. |
| 2011/0042813 | A1 | 2/2011 | Crain et al. |
| 2011/0057168 | A1 * | 3/2011 | Kobayashi ............ B82Y 10/00 257/24 |
| 2011/0104442 | A1 | 5/2011 | Yoon et al. |
| 2011/0210314 | A1 | 9/2011 | Chung et al. |
| 2011/0227000 | A1 | 9/2011 | Ruoff et al. |
| 2011/0309334 | A1 | 12/2011 | Chang et al. |
| 2012/0058350 | A1 | 3/2012 | Long et al. |
| 2012/0107593 | A1 | 5/2012 | Luo et al. |
| 2012/0153262 | A1 | 6/2012 | Paranjape et al. |
| 2012/0214172 | A1 * | 8/2012 | Chen .................. B82Y 15/00 435/6.19 |
| 2012/0220053 | A1 | 8/2012 | Lee et al. |
| 2013/0040283 | A1 | 2/2013 | Star et al. |
| 2014/0159040 | A1 | 6/2014 | Dimitrakipoulos et al. |
| 2014/0162375 | A1 | 6/2014 | Afzali-Ardakani et al. |

OTHER PUBLICATIONS

Chang et al "Single-walled carbon nanotube field-effect transistor with graphene oxide passivation for fast, sensitive and selective protein detection" Biosensors and Bioelectronics, Oct. 23, 2012, 42: 186-192. (Year: 2012).*
Abe, M. et al. "Quantitative Detection of Protein using a Top-gate Carbon Nanotube Field Effect Transistor," (2007) The Journal of Physical and Colloid Chemistry 111, 8667.
Akca et al., "Competing Interactions in DNA Assembly on Graphene," Plos One 2011, 6, e18442.
Allen, B.L. et al. "Carbon Nanotube Field-Effect-Transistor-Based Biosensors," (2007) Advanced Materials 19, 1439-1451.
An et al., "High-Performance Flexible Graphene Aptasensor for Mercury Detection in Mussels," ACS Nano 2013, 7, 10563-10571.
Aragay, G. et al., "Recent Trends in Macro-, Micro-, and Nanomaterial-Based Tools and Strategies for Heavy-Metal Detection," Chemical reviews (2011) 111, 3433-58.
Avasarala, B. et al. "Electrochemical oxidation behavior of titanium nitride based electrocatalysts under PEM fuel cell conditions," Electrochimica Acta (2010) p. 9024-9034, 55.
Avouris, P., "Graphene: Electronic and Photonic Properties and Devices," Nano Lett. (2010) 10, 4285-4294.
Bae, S. Y. et al., "Large-Area Graphene Films by Simple Solution Casting of Edge—Selectively Functionalized Graphite," Acs Nano (2011) 5, 4974-4980.
Bae, S., et al., "Roll-to-Roll Production of 30-Inch Graphene Films for Transparent Electrodes," Nat Nanotechnol (2010) 5, 574-578.
Bansi, Z. B. et al., "A Novel Label-Free Optical Biosensor Using Synthetic Oligonucleotides from *E. coli* O157:H7: Elementary Sensitivity Tests," Sensors-Basel (2009) 9, 4890-4900.
Bedioui, F. et al. "Comment on Electrochemical Detection of Peroxynitrite Using a Biosensor Based on a Conducting Polymer—Manganese Ion Complex," Analytical Chemistry (2011) p. 5463-5464, 83.

Benayad, A. et al., "Controlling Work Function of Reduced Graphite Oxide with Au—Ion Concentration," Chem. Phys. Lett. (2009) 475, 91-95.
Beqa L.et al., "Gold Nanoparticle-Based Simple Colorimetric and Ultrasensitive Dynamic Light Scattering Assay for the Selective Detection of Pb(li) from Paints, Plastics, and Water Samples," ACS applied materials & interfaces (2011) 3, 668-673.
Bloxham, M. J. et al, "Determination of Mercury in Filtered Sea-Water by Flow Injection with on-Line Oxidation and Atomic Fluorescence Spectrometric Detection," J. Anal. At. Spectrom (1996) 11, 511-514.
Bolotin, K. I. et al., "Ultrahigh Electron Mobility in Suspended Graphene," Solid State Communications (2008) 146, 351-355.
Boyanov, M. I. et al., "Mechanism of Pb Adsorption to Fatty Acid Langmuir Monolayers Studied by X-Ray Absorption Fine Structure Spectroscopy," The Journal of Physical Chemistry B (2003) 107,9780-9788.
Braun, C. et al. "Ca3N2 and Mg3N2: Unpredicted High-Pressure Behavior of Binary Nitrides," Journal of the American Chemical Society (2011) p. 4307-4315, 133.
Bunch, J.S. et al. "Electrochemical Resonators from Graphene Sheets," (2007) Science 315, 490.
Burg, B. R. et al., "High-Yield Dielectrophoretic Assembly of Two-Dimensional Graphene Nanostructures," Appl. Phys. Lett. (2009) 94.
Campos-Delgado, J. et al. "Bulk Production of a New Form of sp2 Carbon: Crytalline Graphene Nanoribbons," Nano Letters (2008) p. 2773-2778, 8, 9.
Cao, A. et al. "Afacile One-step Method to Produce Grraphene-CdS Quantum Dot Nancomposites as Promising Optoelectronic Materials," Advanced Materials (2010) p. 103-106, 22.
Carro, P. et al., "Mechanisms of Defect Generation and Clustering in Ch3s Self-Assembled Monolayers on Au(111)," J Phys Chem Lett (2012) 3, 2159-2163.
Chai, F.et al., "Colorimetric Detection of Pb2+ Using Glutathione Functionalized Gold Nanoparticles," ACS applied materials & interfaces (2010) 2, 1466-1470.
Chakraborty, S. et al. "Amperometric biosensing of glutamate using carbon nanotube based electrode," Electrochemistry Communications, (2007) p. 1323-1330, 9.
Chang et al. "High-Performance, Highly Bendable MoS2 Transistors with High-K Dielectrics for Flexible Low-Power Systems," Acs Nano, 2013, 7, 5446-5452.
Chang, J. B. et al., "Ultrasonic-Assisted Self-Assembly of Monolayer Graphene Oxide for Rapid Detection of *Escherichia coli* Bacteria," Nanoscale (2013) 5, 3620-3626.
Chen, J. H., "Controlled Decoration of Carbon Nanotubes with Nanoparticles," Nanotechnology (2006) 17, 2891-2894.
Chen, J. L. et al., "A Functionalized Gold Nanoparticles and Rhodamine 6g Based Fluorescent Sensor for High Sensitive and Selective Detection of Mercury(li) in Environmental Water Samples," Anal. Chim. Acta (2007) 599, 134-142.
Chen, J.H. et al. "Intrinsic and Extrinsic Performance Limits of Graphene Devices on SiO2," (2008) Nature Nanotechnology 3, 206.
Chen, K. et al., "Hg(li) Ion Detection Using Thermally Reduced Graphene Oxide Decorated with Functionalized Gold Nanoparticles," Analytical chemistry 2012, 84, 4057-62.
Chen, K. H. et al., "C-Erbb-2 Sensing Using Algan/Gan High Electron Mobility Transistors for Breast Cancer Detection," Appl. Phys. Lett. (2008) 92.
Chen, K. H. et al., "Low Hg(li) Ion Concentration Electrical Detection with Algan/Gan High Electron Mobility Transistors," Sens. Actuators B (2008) 134, 386-389.
Chen, R.J. et al. "Noncovalent functionalization of carbon nanotubes for highly specific electronic biosensors," (2003) Proceedings of the National Academy of Sciences 100,9, 4984-4989.
Chen, X. et al. "Synthesis of "clean" and well-dispersive Pd Nanoparticles with excellent electrocatalytic property on graphene oxide," Journal of the American Chemical Society (2011) p. 3693-3695, 133.
Cheng, M. S. et al., "Membrane-Based Electrochemical Nanobiosensor for *Escherichia coli* Detection and Analysis of Cells Viability," Environ. Sci. Technol. (2011) 45, 6453-6459.

(56) References Cited

OTHER PUBLICATIONS

Choucair, M. et al. "Gram-scale production of graphene based on solvothermal synthesis and sonication," Nature Nanotechnology (2009) p. 30-33, 4.
Ci, L. et al. "Controlled Nanocutting of Graphene," Nano Research (2008) p. 116-122, 1.
Compton, O. C., "Graphene Oxide, Highly Reduced Graphene Oxide, and Graphene: Versatile Building Blocks for Carbon-Based Materials," Small (2010) 6, 711-723.
Costa, H. O. et al., "Is there a relationship between the pH and volume of saliva and esophageal pH-metry results," Dysphagia (2005) 20 (3), 175-181.
Cote, L.J. et al. "Flash Reduction and Patterning of Graphite Oxide and Its Polymer Composite," Journal of the American Chemistry Society (2009) p. 11027-11033, 131.
Cui, Y et al. "Nanowire Nanosensors for Highly Sensitive and Selective Detection of Biological and Chemical Species," (2001) Science 293, 1289-1292.
Dan, Y. et al., "Intrinsic Response of Graphene Vapor Sensors," Nano Lett (2009) 9, 1472-1475.
Dash et al., "Bioremediation of mercury and the importance of bacterial mer genes," Int Biodeter Biodegr 2012, 75, 207-213.
Dikin, D.A. et al. "Preparation and Characterization of Graphene Oxide Paper," Nature (2007) p. 457-461, 448.
Dong, X.C. et al. "Electrical Detection of DNA Hybridization with Single-Base Specificity using Transistors Based on CVD-Grown Graphene Sheets," (2010) Advanced Materials 22, 1.
Dong, X.C. et al. "Electrical Detection of Femtomolar DNA via Gold-Nanoparticle Enhancement in Carbon-Nanotube-Network Field-Effect Transistors," (2008) Advanced Materials 20, 2389-2393.
Du, X. et al. "Approaching ballistic transport in suspended graphene," Nature Nanotechnology (2008) p. 491-497, 5.
El-Serag, H. B. et al., "Update on the epidemiology of gastro-oesophageal reflux disease: a systematic review," Gut (2014) 63 (6), 871-880.
Farrow, B. et al. "CdSe Quantum Dot Sensitized Solar Cells. Shuttling Electrons Through Stacked Carbon Nanocups," Journal of the American Chemical Society (2009) p. 11124-11131, 131.
Fischer, A. et al. "Synthesis of Ternary Metal Nitride Nanoparticles Using Mesoporous Carbon Nitride as Reactive Template," ACS Nano (2008) p. 2489-2496, 2, 12.
Forzani, E. S. et al., "Tuning the Chemical Selectivity of Swnt-Fets for Detection of Heavy-Metal Ions," Small (2006) 2, 1283-1291.
Fowler, J. D. et al., "Hydrogen Detection by Polyaniline Nanofibers on Gold and Platinum Electrodes," The Journal of Physical Chemistry C (2009) 113, 6444-6449.
Fowler, J. D. et al., "Practical Chemical Sensors from Chemically Derived Graphene," ACS Nano (2009) 3, 301-306.
Fratamico, P. M. et al., "Detection of *Escherichia coli* O157:H7 in Food Using Real-Time Multiplex Pcr Assays Targeting the Stx(1), Stx(2), Wzy(O157), and the Flic(H7) or Eae Genes," Food Anal Method (2010) 3, 330-337.
Gao et al. "Crystallographic Tailoring of Graphene by Nonmetal SIO2 Nanoparticles," Journal of the American Chemical Society (2009) p. 13934-13936, 131.
Gao et al., "Subthreshold Regime Has the Optimal Sensitivity for Nanowire Fet Biosensors," Nano letters (2010) 10, 547-552.
Gasparik, J. et al., "Concentration of Lead, Cadmium, Mercury and Arsenic in Leg Skeletal Muscles of Three Species of Wild Birds," Journal of Environmental Science and Health, Part A (2010) 45, 818-823.
Geim, A. K. et al., "The Rise of Graphene. Nat. Mater," (2007) 6, 183-191.
Geim, A.K. "Graphene: Status and Prospects," Science (2009).
Geng, D. et al. "High Oxygen-Reduction Activity and Durability of Nitrogen-Doped Graphene," Energy and Environmental Science (2011) p. 760-764, 4.
Giardi, M.T. et al. "Optical biosensors for environmental monitoring based on computational and biotechnological tools for engineering the photosynthetic D1 protein of *Chiamydomonas reinhardtii*," Biosensors and Bioelectronics (2009) p. 294-300, 25, 2.
Gilje, S. et al., "A Chemical Route to Graphene for Device Applications," Nano Lett. (2007) 7, 3394-3398.
Gomez-Navarro, C. et al., "Electronic Transport Properties of Individual Chemically Reduced Graphene Oxide Sheets," Nano Lett (2007) 7, 3499-3503.
Gracias, K. S. et al., "A Review of Conventional Detection and Enumeration Methods for Pathogenic Bacteria in Food," Can. J. Microbiol. (2004) 50, 883-890.
Guijarro, N. et al. "Direct Correlation between Ultrafast Injection and Photoanode Performance in Quantum of Sensitized Solar Cells," Journal of Physical Chemistry (2010) p. 22352-22360, 114.
Guo, C.X. et al. "Layered Graphene/Quantum Dots for Photovoltaic Devices," Angewandte Chemie International Edition (2010) p. 3014-3017, 49.
Guo, S. et al. "Three-Dimensional Pt-onPd Bimetallic Nanodendrites Supported on Graphene Nanosheet: Facile Synthesis and Used as an Advanced Nanoelectrocatalyst for Methanol Oxidation," ACS Nano, (2010) p. 547-555, 4, 1.
He et al., "Quenching the Chemiluminescence of Acridinium Ester by Graphene Oxide for Label-Free and Homogeneous DNA Detection," Acs Appl Mater Inter 2013, 5, 11336-11340.
He et al., "An ultra-high sensitive platform for fluorescence detection of micrococcal nuclease based on graphene oxide," Biosens Bioelectron 2013, 42, 467-473.
Heidelbaugh, J. J. et al., "Magnitude and Economic Effect of Overuse of Antisecretory Therapy in the Ambulatory Care Setting," Am J Manag Care (2010) 16(9), E228-E234.
Higgins, V.J. "Application of genome-wide expression analysis to identify molecular markers useful in monitoring industrial fermentations," Applied and Environmental Microbiology (2003) p. 7535-7540, 69.
Hilder, M. et al., "Direct Electro-Deposition of Graphene from Aqueous Suspensions," Phys Chem Chem Phys (2011) 13, 9187-9193.
Ho, T.-Y. et al., "Determination of Trace Metals in Seawater by an Automated Flow Injection Ion Chromatograph Pretreatment System with lcpms," Talanta (2010) 82, 1478-1484.
Hong, S. et al "A Flexible Approach to Mobility," (2007) Nature Nanotechnology 2, 207.
U.S. Environmental Protection Agency, <http://www.epa.gov/> webpage available at least as early as Apr. 18, 1997.
Hu, P.A. et al. "Carbon Nanostructure-Based Field-Effect Transistors for Label-Free Chemical/Biological Sensors," (2010) p. 5133-5159, 10.
Huang, B. et al., "Adsorption of Gas Molecules on Graphene Nanoribbons and Its Implication for Nanoscale Molecule Sensor," J. Phys. Chem. C (2008) 112, 13442-13446.
Huang, C.-C., "Selective Gold-Nanoparticle-Based "Turn-on" Fluorescent Sensors for Detection of Mercury(li) in Aqueous Solution," Anal. Chem. (2006) 78, 8332-8338.
Huang, Y. X. et al., "Graphene-Based Biosensors for Detection of Bacteria and Their Metabolic Activities," J. Mater. Chem. (2011) 21, 12358-12362.
Hummers, W. et al. "Preparation of Graphitic Oxide," (1958) American Chemistry Society 80, 1339.
Hwang, J., "Transport Properties of a DNA-Conjugated Single-Wall Carbon Nanotube Field-Effect Transistor," Jpn J Appl Phys (2009) 48, 06FD08.
Ishigami, M. et al., "Atomic Structure of Graphene on Sio2," Nano Lett (2007) 7, 1643-1648.
Ishikawa et al, "A Calibration Method for Nanowire Biosensors to Suppress Device-to-Device Variation," ACS Nano (2009) 3, 3969-3976.
Ishikawa, F. N. et al., "Importance of Controlling Nanotube Density for Highly Sensitive and Reliable Biosensors Functional in Physiological Conditions," Acs Nano (2010) 4, 6914-6922.
Jain, K.K. "Applications of Nanobiotechnology in Clinical Diagnostics," Clinical Chemistry (2007) p. 2002-2009, 53, 11.
Jiang, Q.W. et al. "Highly ordered TiN nantube arrays as counter electrodes for dye-sensitized solar cells," Chemical Communications (2009) p. 6720-6722.

(56) References Cited

OTHER PUBLICATIONS

Jiang, Q.W. et al. "Surface-Nitrided nickel with bifunctional structure as low-cost counter electrode for dye-sensitized solar cells," Journal of Physical Chemistry C (2010) p. 13397-13401, 114.

Jiang, S. et al., "Real-Time Electrical Detection of Nitric Oxide in Biological Systems with Sub-Nanomolar Sensitivity," Nature communications (2013) 4, 2225.

Jun, Y. et al. "A general phase-transfer protocol for metal ions and its application in nanocrystal synthesis," Nature Materials (2009) p. 683-689, 8.

Jun, Y.S. et al. "Mesoporous, 2D Hexagonal Carbon Nitride and Titanium Nitride/Carbon Composites," Advanced Materials (2009) p. 4270-4274, 21.

Jung, I. et al. "Tunable Electrical Conductivity of Individual Graphene Oxide Sheets Reduced at "Low" Temperatures," (2008) Nano Letters 8, 4283.

Kang, B. S. et al., "Electrical Detection of Deoxyribonucleic Acid Hybridization with Algan/Gan High Electron Mobility Transistors" Appl. Phys. Lett. (2007) 89.

Karunasagar, D. et al., "Development of a 'Collect and Punch' Cold Vapour Inductively Coupled Plasma Mass Spectrometric Method for the Direct Determination of Mercury at Nanograms Per Litre Levels," J. Anal. At. Spectrom (1998) 13, 679-682.

Kawahara, H. et al., "Physiological analysis of the effects of rikkunshito on acid and non-acid gastroesophageal reflux using pH-multichannel intraluminal impedance monitoring," Pediatr Surg Int (2014) 30 (9), 927-931.

Kawasaki, S. et al., "Evaluation of a Multiplex Pcr System for Simultaneous Detection of *Salmonella* Spp., *Listeria* Monocytogenes, and *Escherichia coli* O157:H7 in Foods and in Food Subjected to Freezing," Foodborne Pathog Dis (2009) 6, 81-89.

Kim, J. P. et al, "Enhancement of Sensitivity and Specificity by Surface Modification of Carbon Nanotubes in Diagnosis of Prostate Cancer Based on Carbon Nanotube Field Effect Transistors," Biosens Bioelectron (2009) 24, 3372-3378.

Kim et al., "Highly Selective Environmental Nanosensors Based on Anomalous Response of Carbon Nanotube Conductance to Mercury Ions," Phys. Chem., 2009, 113, 19393-19396.

Knopfmacher et al., "Nernest Limit in Dual-Gated Si-Nanowire FET Sensors," Nano Lett, 2010, 10, 2268-2274.

Kobayashi, T. et al., "Channel-Length-Dependent Field-Effect Mobility and Carrier Concentration of Reduced Graphene Oxide Thin-Film Transistors," Small (2010) 6, 1210-1215.

Kong, B.S. et al. "Layer-by-Layer assembly of graphene and gold nanoparticles by vacuum filtration and spontaneous reduction of gold ions," Chemical Communications (2009) p. 2174-2176.

Kovtyukhova, N. et al. "Layer-by-Layer Assembly of Ultrathin Composites Films from Micron-Sized Graphite Oxide Sheets and Polycations," (1999) Chemistry Materials 11, 771-778.

Kurkina, T. et al., "Self-Assembled Electrical Biodetector Based on Reduced Graphene Oxide," Acs Nano (2012) 6, 5514-5520.

Kwon, K. C. et al., "Work-Function Decrease of Graphene Sheet Using Alkali Metal Carbonates," The Journal of Physical Chemistry C (2012) 116, 26586-26591.

Kwon, O. S. et al., "Flexible Fet-Type Vegf Aptasensor Based on Nitrogen-Doped Graphene Converted from Conducting Polymer," Acs Nano (2012) 6, 1486-1493.

Langford, J.I. et al. "Scherrer after Sixty Years: A Survey and Some New Results in the Determination of Crystallite Size," (1978) Journal of Applied Crystallography 11, 102-113.

Lee, B. Y. et al., "Universal Parameters for Carbon Nanotube Network-Based Sensors: Can Nanotube Sensors Be Reproducible?," Acs Nano (2011) 5, 4373-4379.

Lee, N. J. et al., "The Interlayer Screening Effect of Graphene Sheets Investigated by Kelvin Probe Force Microscopy," Appl. Phys. Lett. (2009) 95.

Lee, S.M. et al. "Expression of heat shock protein and hemoglobin genes in Chironomus tentans (Diptera, chironomidae) larvae exposed to various environmental pollutants: A potential biomarker of freshwater monitoring," Chemosphere (2006) p. 1074-1081, 65.

Leopold, K. et al., "Methods for the Determination and Speciation of Mercury in Natural Waters—a Review," Anal Chim Acta (2010) 663, 127-138.

Lerner et al., "Detecting Lyme disease using antibody-functionalized single-walled carbon nanotube transistors," Biosens Bioelectron, 2013, 45, 163-167.

Li J. et al. "Carbon Nanotube Nanoelectrode Array for Ulttrasensitive DNA Detection," (2003) Nano Letters 3,5, 597-602.

Li, B. R. et al, "Biomolecular Recognition with a Sensitivity-Enhanced Nanowire Transistor Biosensor," Biosens Bioelectron (2013) 45, 252-259.

Li, G.R. et al. "Carbon nanotubes with titanium nitride as a low-cost counter-electrode material for dye-sensitized solar cells," Angewandte Chemie (2010) p. 3653-3656, 49.

Li, M. et al., "Detection of Lead (li) with a "Turn-on" Fluorescent Biosensor Based on Energy Transfer from Cdse/Zns Quantum Dots to Graphene Oxide," Biosensors and Bioelectronics (2013) 43, 69-74.

Li, T. et al., "Lead(li)-Induced Allosteric G-Quadruplex Dnazyme as a Colorimetric and Chemiluminescence Sensor for Highly Sensitive and Selective Pb2+ Detection," Analytical chemistry (2010) 82, 1515-1520.

Li et al., "Label-Free Colorimetric Detection of Aqueous Mercury Ion (Hg2+) Using Hg2+-Modulated G-Quadruplex-Based DNAzymes," Anal Chem 2009, 81, 2144-2149.

Li, W. W. et al., "Reduced Graphene Oxide Electrically Contacted Graphene Sensor for Highly Sensitive Nitric Oxide Detection," Acs Nano (2011) 5, 6955-6961.

Li, X. et al. "Chemically derived, ultrasmooth graphene nanoribbon semiconductors," Science (2008) p. 1229-1232, 319, 5867.

Li, X. et al. "Simultaneous nitrogen-doping and reduction of graphene oxide," Journal of the American Chemical Society (2009) p. 15939-15944, 131.

Li et al., "A "turn-on" fluorescent sensor for detection of Pb2+ based on graphene oxide and G-quadruplex DNA," Phys Chem Chem Phys, 2013, 15, 12800-12804.

Li, Z. et al. "Low temperature growth of graphene by chemical vapor deposition using solid and liquid carbon sources.", Journal of the American Chemical Society (2011) p. 3385-3390, 5, 4.

Li, Z. Y. et al., "An Applied Approach in Detecting *E. coli* O157:H7 Using Immunological Method Based on Chemiluminescence and Magnetic Nanoparticles," Acta Chim. Sinica (2010) 68, 251-256.

Lin, Y.M. et al. "Operation of Graphene Transistors at Gigahertz Frequencies," (2009) Nano Letters 9, 422.

Liu, J. et al., "Stimuli-Responsive Disassembly of Nanoparticle Aggregates for Light-up Colorimetric Sensing," Journal of the American Chemical Society (2005) 127,12677-12683.

Liu et al., "Rational design of "turn-on" allosteric DNAzyme catalytic beacons for aqueous mercury ions with ultrahigh sensitivity and selectivity," Angew Chem Int Edit 2007, 46, 7587-7590.

Lu J. et al. "Nanometal -Decorated Exfoliated Graphite Nanoplatelet Based Glucose Biosensors with High Sensitivity and Fast Response," (2008) ACS Nano 2, 1825.

Lu, G. H. et al., "Electrostatic-Force-Directed Assembly of Ag Nanocrystals onto Vertically Aligned Carbon Nanotubes," J. Phys. Chem. C (2007) 111, 17919-17922.

Lu, G. H. et al., "Gas Detection Using Low-Temperature Reduced Graphene Oxide Sheets," Appl. Phys. Lett. (2009) 94, 083111.

Lu, G. H. et al., "Room-Temperature Gas Sensing Based on Electron Transfer between Discrete Tin Oxide Nanocrystals and Multiwalled Carbon Nanotubes," Adv. Mater. (2009) 21, 2487-2491.

Lu, G. H., "Toward Practical Gas Sensing with Highly Reduced Graphene Oxide: A New Signal Processing Method to Circumvent Run-to-Run and Device-to-Device Variations," ACS Nano (2011) 5, 1154-1164.

Lu, G.H. et al. "Electrostatic-Force-Directed Assembly of Ag Nanocrystals onto Vertically Aligned Carbon Nanotubes," (2007) Journal of Physical Chemistry C 11, 17919.

Lu, G.H. et al. "Facile, Noncovalent Decoration of Graphene Oxide Sheets with Nanocrytals," (2009) Nano Research 2, 192-200.

Luo, L. B. et al, "Silicon Nanowire Sensors for Hg2+ and Cd2+ Ions," Appl. Phys. Lett. (2009) 94, 193101.

(56) References Cited

OTHER PUBLICATIONS

Ma, X. F. et al., "Crumpled Nanopaper from Graphene Oxide," Nano Lett. (2012) 12, 486-489.
Mah, V. et al., "Lead(li) Complex Formation with Glutathione," Inorg Chem (2012) 51, 6285-98.
Mahajan, R. K. et al., "A Mercury(li) Ion-Selective Electrode Based on Neutral Salicylaldehyde Thiosemicarbazone," Talanta (2003) 59, 101-105.
Majid, E. et al., "Boron Doped Diamond Biosensor for Detection of *Escherichia coli*," J. Agric. Food Chem. (2008) 56, 7691-7695.
Mandal, H. S.et al., "Carbon Nanotube Thin Film Biosensors for Sensitive and Reproducible Whole Virus Detection," Theranostics (2012) 2, 251-257.
Manna et al., "Theoretical understanding of single-stranded DNA assisted dispersion of graphene," J Mater Chem B 2013, 1, 91-100.
Mao, S. et al. "Highly Sensitive Protein Sensor Based on Thermally-Reduced Graphene Oxide Field-Effect Transistor," (2011) Nano Research 4, 10, 921-930.
Mao, S. et al. "Protein viability on Au Nano particles during an Electrospray and Electrostaic-Force-Directed Assembly Process," Journal of Nanomaterials (2010) 6.
Mao, S. et al., "Coating Carbon Nanotubes with Colloidal Nanocrystals by Combining an Electrospray Technique with Directed Assembly Using an Electrostatic Field," Nanotechnology (2008) 19, 455610.
Mao, S. et al., "Direct Growth of Vertically-oriented Graphene for Field-Effect Transistor Biosensor," Sci Rep-Uk 2013, 3.
Mao, S. et al., "Specific Protein Detection Using Thermally Reduced Graphene Oxide Sheet Decorated with Gold Nanoparticle-Antibody Conjugates," Adv. Mater (2010) 22, 3521-3526.
Mao et al., "Specific Biosensing Using Carbon Nanotubes Functionalized with Gold Nanoparticle-Antibody Conjugates," Carbon 2010, 48, 479-486.
Marcano, D. C. et al., "Improved Synthesis of Graphene Oxide," Acs Nano (2010) 4, 4806-4814.
Markets and Markets, "Smar/Intelligent Sensor Market by Type (flow Sensor, Dissolved Oxygen Sensor, Temperature Sensor, Pressure Sensor, Touch Sensor), Technology (MEMS, CMOS), Application (Aerospace, Automotive, Industrial, building Automation), & by Geography—Forecasts & Analysis to 2013-2020," http://www.marketsandmarkets.com/Market-Reports/smart-sensor-market-43119772.html (2014).
Martinez, M.T. et al. "Label-Free DNA Biosensors Based on Functionalized Carbon Nanotube Field Effect Transistors," (2009) Nano Letters 9,2, 530-536.
McAllister, M. J. et al., "Single Sheet Functionalized Graphene by Oxidation and Thermal Expansion of Graphite," Chem. Mater. (2007) 19, 4396-4404.
Meyer, J. C. et al., "The Structure of Suspended Graphene Sheets," Nature (2007) 446, 60-3.
Mohamed Ali, E. et al., "Ultrasensitive Pb2+ Detection by Glutathione-Capped Quantum Dots," Analytical chemistry (2007) 79, 9452-9458.
Mohanty, N. et al., "Graphene-Based Single-Bacterium Resolution Biodevice and DNA Transistor: Interfacing Graphene Derivatives with Nanoscale and Microscale Biocomponents," Nano Lett. (2008) 8, 4469-4476.
Morton J. et al., "Detection of Trace Heavy Metal Ions Using Carbon Nanotube-Modified Electrodes," Electroanalysis (2009) 21, 1597-1603.
Murakami, T. N. et al. "Highly Efficient Dye-Sensitized Solar Cells Based on Carbon Black Counter Electrodes," Journal of the Electrochemical Society, (2006) p. A2255-A2261, 153, 12.
Muszynski, R. et al, "Decorating Graphene Sheets with Gold Nanoparticles," J. Phys. Chem. C (2008) 112, 5263-5266.
"New Drinking Water Rules, Goals Proposed," Chemical & Engineering News Archive (1985) 63, 6.
Ni, Z.H. et al. "Probing Charged Impurities in Suspended Graphene Using Raman Spectroscopy," (2009) ACS Nano 3, 569.
Novoselov, K.S. et al. "Electric Field Effect on Atomically Thin Carbon Films," (2004) Science 306, 666.

Office Action from the US Patent and Trademark Office for U.S. Appl. No. 13/399,288 dated May 4, 2015 (8 pages).
Office Action from the US Patent and Trademark Office for U.S. Appl. No. 13/399,288 dated Nov. 14, 2014 (8 pages).
Ohno, Y. et al. "Electrolyte-Gated Graphene Field-Effect Transistors for Detecting pH and Protein Adsorption," (2009) Nano Letters 9, 3318.
Ouyang, Y. J. et al. "Projected performance advantage of multilayer graphene nanoribbons as a transistor channel material," Nano Res., (2010) p. 8-15, 3.
Park, S. et al. "Colloidal Suspensions of Highly Reduced Graphene Oxide in a Wide Variety of Organic Solvents," Nano Letters (2009) p. 1593-1597, 9, 4.
Park, S. et al., "Chemical Methods for the Production of Graphenes," Nat Nanotechnol (2009) 4, 217-224.
Park et al., "Ultrasensitive Flexible Graphene Based Field-Effect Transistor (FET)-Type Bioelectronic Nose," Nano Lett (2012) 12, 5082-5090.
Park, S., "Aqueous Suspension and Characterization of Chemically Modified Graphene Sheets," Chem. Mater (2008) 20, 6592-6594.
Patchkovskii, S. et al. "Graphene Nanstructures as Tunable Storage Media for Molecular Hydrogen," (2005) Proceedings in the National Academy of Science 102, 10439.
Pavlish, J. H. et al., "State Review of Mercury Control Options for Coal-Fired Power Plants. Fuel Process," Technol (2003) 82, 89-165.
PCT/US2015/043449 International Search Report and Written Opinion dated Oct. 28, 2015 (10 pages).
PCT/US2015/043449 International Preliminary Report on Patentability dated Feb. 16, 2017 (8 pages).
Pereira, A.C. et al. "Amperometric biosensor for lactate based on lactate dehydrogenase and Meldola Blue coimmobilized on multiwall carbon-nanotube," Sensor and Actuators B (2006) p. 269-276, 124.
Petersen, M. et al. "Improving the Efficiency of FP-LAPW Calculations," (2000) Computer Physics Communications 126-294.
Ponomarenko, L.A. et al. "Chaotic Dirac Billiard in Graphene Quantum Dots," (2008) Science 320, 356.
Puk, R. et al., "Determination of Mercury(li), Monomethylmercury Cation, Dimethylmercury and Diethylmercury by Hydride Generation, Cryogenic Trapping and Atomic-Absorption Spectrometric Detection," Anal. Chim. Acta (1994) 292, 175-183.
Qazi, M. et al. "Trace Gas Detection using Nanostructured Graphite Layers," (2007) Applied Physics Letters 91, 3.
Quinlin, R. A. et al., "Transfer of Carbon Nanosheet Films to Nongrowth," Zero Thermal Budget Substrates. J Vac Sci Technol B (2011) 29, 030602.
Rao, C. N. et al, "Graphene: The New Two-Dimensional Nanomaterial," Angew Chem Int Ed Engl (2009) 48, 7752-77.
Reina, A. et al. "Growth of large-area single- and bi-layer graphene by controlled carbon precipitation on polycrystalline Ni surfaces," Nano Research (2009) p. 509-516, 2.
Reuven et al., "Thiol modification of silicon-substituted hydroxyapatite nanocrystals facilitates fluorescent labelling and visualization of cellular internalisation," J Mater Chem B 2013, 1, 3926-3931.
Richardson, S. D., "Environmental Mass Spectrometry: Emerging Contaminants and Current Issues," Anal. Chem. (2012) 84, 747-778.
Richardson, S. D. et al., "Water Analysis: Emerging Contaminants and Current Issues," Anal. Chem. (2011) 83, 4614-4648.
Robinson, J. T. et al., "Wafer-Scale Reduced Graphene Oxide Films for Nanomechanical Devices," Nano letters (2008) 8, 3441-3445.
Russell, J. et al. "Configuration-sensitive molecular sensing on doped graphene sheets," Nano Research (2010).
Satija, J. et al. "Emerging use of nanostructure films containing capped gold nanoparticles in biosensors," Nanotechnology, Science and Applications (2010) p. 171-188, 3.
Schedin, F. et al, "Detection of Individual Gas Molecules Adsorbed on Graphene," Nat. Mater (2007) 6, 652-655.
Scherrer, P. et al "Bestimmung der Grosse und der inneren Struktur von Kolloidteilchen mittels Rontgenstrahlen," (1918) Nachr. Ges. Wiss. Gottingen 26, 98-100.

(56) References Cited

OTHER PUBLICATIONS

Sen, K. et al., "Development of a Sensitive Detection Method for Stressed *E. coli* O157:H7 in Source and Finished Drinking Water by Culture-Qpcr," Environ. Sci. Technol. (2011) 45, 2250-2256.

Shan, C.S. et al. "Direct Electrochemistry of Glucose Oxidase and Biosensing for Glucose Based on Graphene," (2009) Analytical Chemistry 81, 2378.

Shan, C.S. et al. "Graphene/AuNPs/chitosan nanocomposites film for glucose biosensing," Biosensors and Bioelectronics (2010) p. 1070-1074, 25.

Sharf et al., "Origins of Charge Noise in Carbon Nanotube Field-Effect Transistor Biosensors," Nano Lett 2012, 12, 6380-6384.

Shukla, G. S. et al., "The Present Status of Biological Effects of Toxic Metals in the Environment: Lead, Cadmium, and Manganese," Canadian Journal of Physiology and Pharmacology (1984) 62, 1015-1031.

Simonian, A.L. et al. "FET-Based Biosensors for the Direct Detection of Organophosphate Neurotoxins," Electroanalysis (2004) p. 1896-1906, 16, 22.

Singh, A. K. et al., "Gold Nanorod Based Selective Identification of *Escherichia coli* Bacteria Using Two-Photon Rayleigh Scattering Spectroscopy," Acs Nano (2009) 3, 1906-1912.

Singh, J. et al, "A Scorpion Probe-Based Real-Time Pcr Assay for Detection of *E-coli* O157:H7 in Dairy Products," Foodborne Pathog Dis (2009) 6, 395-400.

Singh, J. et al., "A Molecular Beacon-Based Duplex Real-Time Polymerase Chain Reaction Assay for Simultaneous Detection of *Escherichia coli* O157:H7 and Listeria Monocytogenes in Milk and Milk Products," Foodborne Pathog Dis (2009) 6, 1195-1201.

Sofo, J.O. et al. "Graphane: a two-dimensional hydrocarbon," (2007) Physical Review 75, 4.

Song, P. et al., "Synthesis of Graphene Nanosheets Via Oxalic Acid-Induced Chemical Reduction of Exfoliated Graphite Oxide," Rsc Adv (2012) 2, 1168-1173.

Sridhar, V. et al., "Defect-Engineered Three-Dimensional Graphene-Nanotube-Palladium Nanostructures with Ultrahigh Capacitance," ACS Nano (2012) 6, 10562-10570.

Stankovich, S. et al., "Stable Aqueous Dispersions of Graphitic Nanoplatelets Via the Reduction of Exfoliated Graphite Oxide in the Presence of Poly(Sodium 4-Styrenesulfonate)," J. Mater. Chem. (2006) 16, 155-158.

Star, A et al. "Electronic Detection of Specific Protein Binding Using Nanotube FET Devices," (2003) Nano Letters 3,4, 459-463.

Su et al., "Nanomaterials-based sensors for applications in environmental monitoring," J Mater Chem 2012, 22, 18101-18110.

Sudibya, H. G. et al, "Electrical Detection of Metal Ions Using Field-Effect Transistors Based on Micropatterned Reduced Graphene Oxide Films," Acs Nano (2011) 5, 1990-1994.

Sun, D. F. et al., "High Performance Supercapacitor Electrode Based on Graphene Paper Via Flame-Induced Reduction of Graphene Oxide Paper.," J. Power Sources (2013) 222, 52-58.

Swearingen, C. B. et al., "Immobilization of a Catalytic DNA Molecular Beacon on Au for Pb(li) Detection," Analytical chemistry (2004) 77, 442-448.

Thotiyl, M.M. et al. "Pd Supported on Titanium Nitride for Efficient Ethanol Oxidation," Journal of Physical Chemistry C (2010) p. 17934-17941, 114.

Trung, T. Q. et al, "High Thermal Responsiveness of a Reduced Graphene Oxide Field-Effect Transistor," Adv. Mater. (2012) 24, 5254-5260.

Unni et al., "Redox-Mediated Synthesis of Functionalised Graphene: A Strategy towards 2D Multifunctional Electrocatalysts for Energy Conversion Applications," Chempluschem 2013, 78, 1296-1303.

Vicarelli, L. et al., "Graphene Field-Effect Transistors as Room-Temperature Terahertz Detectors," Nat. Mater. (2012) 11, 865-871.

Wang, Y. et al., "Bacterial Pathogen Surface Plasmon Resonance Biosensor Advanced by Long Range Surface Plasmons and Magnetic Nanoparticle Assays," Anal. Chem. (2012) 84, 8345-8350.

Wang, B. et el, "High Yield Production of Graphene and Its Improved Property in Detecting Heavy Metal Ions," New Carbon Materials (2011) 26, 31-35.

Wang, C. F. et al., "Simultaneous Reduction and Surface Functionalization of Graphene Oxide Via an Ionic Liquid for Electrochemical Sensors," Chem Commun (2013) 49, 3336-3338.

Wang, D. et al. "Self-assembled TiO-graphene hybrid nanostructures for enhanced Li-Ion insertion," ACS Nano (2009) p. 907-914, 3, 4.

Wang, H. et al. "Solvothermal reduction of chemically exfoliated graphene sheets," Journal of the American Chemical Society (2009) p. 9910-9911, 131.

Wang, L. X. et al., "Detection of *Escherichia coli* O157:H7 and Salmonella in Ground Beef by a Bead-Free Quantum Dot-Facilitated Isolation Method," Int. J. Food Microbiol. (2012) 156, 83-87.

Wang, M. et al. "CoS supercedes Pt as efficient electrocatalyst for triodide reduction in dye-sensitized solar cells," Journal of the American Chemical Society (2009) p. 15976-15977, 131.

Wang, S.G. et al. "High Field Emssion Reproducability and Stability of Carbon Nanosheets and Nanosheet-based Backgated Triode Emission Devices," (2006) Applied Physics Letters 89, 3.

Wang, X. et al. "Transparent, Conductive Graphene Electrodes for Dye-Sensitized Solar Cells," (2008) Nano Letters 8, 323.

Wang, X.J. et al. "Room-temperature defect-engineered spin filter based on a non-magnetic semiconductor," Nature Materials (2009) p. 198-202, 8.

Wang, X.R. et al. "N-Doping of Graphene through Electrothermal Reactions with Ammonia," (2009) Science 324, 768.

Wang, Y. et al. "Application of Graphene-Modified Electrode for Selective Detection of Dopamine," (2009) Electrochemical Communications 11, 889.

Wang et al., "In Situ Live Cell Sensing of Multiple Nucleotides Exploiting DNA/RNA Aptamers and Graphene Oxide Nanosheets," Anal Chem 2013, 85, 6775-6782.

Wang et al., "Label-Free Colorimetric Detection of Lead Ions with a Nanomolar Detection Limit and Tunable Dynamic Range by using Gold Nanoparticles and DNAzyme," Adv Mater 2008, 20, 3263-3267.

Wang et al., "Highly sensitive "turn-on" fluorescent sensor for Hg2+ in aqueous solution based on structure-switching DNA," Chem Commun 2008, 6005-6007.

Wang, Z. et al. "Laterally confined graphene nanosheets and graphene/Sno2 composites as high-rate anode materials for lithium-ion batteries," Nano Research (2010) p. 748-756, 3.

Wassei et al., "Oh, the Places You'll Go with Graphene," Accounts Chem Res 2013, 46, 2244-2253.

Watcharotone, S. et al. "Graphene-Silica Composite Thin Films as Transparent Conductors," (2007) Nano Letters 7, 1888.

Wei, Q. et al. "A novel label-free electrochemical immunosensor based on graphene and thionine nanocomposite," Sensors and Actuators B: Chemical (2010) p. 314-318, 149.

Weinert, M. et al. "FLAPW: Applications and Implementations," (2009) Journall of Physics: Condensed Matter 21, 1-14.

Wen et al., "The electrical detection of lead ions using gold-nanoparticle- and DNAzyme-functionalized graphene device," P. Adv Healthc Mater, 2012, 2, 271-274.

Wen, Z. et al. "Metal nitride.graphene nanohybrids: general synthesis and multifunctional titanium nitride/graphene electrocatalyst," Advanced Materials (2011) p. 5445-5450, 23.

Wohlstadter, J.N. et al. "Carbon Nanotube-Based Biosensor," (2003) Advanced Materials 15,14, 1184-1187.

Wu, G. et al. "High-performance electrocatalysts for oxygen reduction derived from polyaniline, iron, and cobalt," Science (2011) p. 443-447, 332.

Wu, M. et al. "Low-cost molybdenum carbide and tungsten carbide counter electrodes for dye-sensitized solar cells," Angew. Chemie (2011) p. 3520-3524, 50.

Wu, Q. Z. et al., "Biomolecule-Assisted Synthesis of Water-Soluble Silver Nanoparticles and Their Biomedical Applications," Inorg Chem (2008) 47, 5882-5888.

Wu. H. et al. "Glucose biosensor based on immobilization of glucose oxidase in platinum nanoparticles/graphene/chitosan nanocomposite film," Talanta (2009) p. 403-406, 80.

(56) References Cited

OTHER PUBLICATIONS

Xia, F. N. et al., "Graphene Field-Effect Transistors with High on/Off Current Ratio and Large Transport Band Gap at Room Temperature," Nano Lett. (2010) 10, 715-718.
Xia et al., "Ultrafast graphene photodetector," Ultrafast Graphene Photodetector. Nat. Nano (2009) 4, 839-843.
Xu, C. et al. "Deposition of Co3O4 nanoparticles onto exfoliated graphite oxide sheets," Journal of Materials Chemistry (2008) p. 5625-5629, 18.
Yamaguchi et al., "Passivating chemical vapor deposited graphene with metal oxides for transfer and transistor fabrication processes," Appl Phys Lett 2013, 102, p. 143505.
Yang, D. et al. "Chemical Analysis of Graphene Oxide Films after Heat and Chemical Treatments by X-ray Photoelectron and Micro-Raman Spectroscopy," (2009) Carbon 47, 145.
Yang, S. et al. "Fabrication of graphene-encapsulated oxide nanoparticles: towards high-performance anode materials for lithium storage," Angew. Chem. Int. Ed. (2010) p. 8408-8411, 49.
Yang et al., "Large-area, three-dimensional interconnected graphene oxide intercalated with self-doped polyaniline nanofibers as a free-standing electrocatalytic platform for adenine and guanine," J Mater Chem B (2013) 1, 2926-2933.
Zafar et al. "Optimization of pH sensing using silicon nanowire field effect transistors with HfO2 as the sensing surface," Nanotechnology 2011, 22, 405501.
Zahir, F. et al., "Low Dose Mercury Toxicity and Human Health. Environ. Toxicol.," Pharmacol (2005) 20, 351-360.
Zeng, S. W. et al., "A Review on Functionalized Gold Nanoparticles for Biosensing Applications," Plasmonics (2011) 6, 491-506.
Zhang, T., "Self- Assembled 1-Octadecanethiol Monolayers on Graphene for Mercury Detection," Nano Lett (2010) 10, 4738-4741.
Zhang, F. J. et al., "Synthesis and Characterization of Graphene-Based Nanosheets Via Chemical Reduction of Expanded Graphite Oxide," Asian J Chem (2012) 24, 371-376.
Zhao, X.-H. et al., "Graphene—Dnazyme Based Biosensor for Amplified Fluorescence "Turn-on" Detection of Pb2+ with a High Selectivity," Analytical chemistry (2011) 83, 5062-5066.
Zhong, Z. et al. "Nanogold-enwrapped graphene naocomposites as trace labels for sensitivity enhancement of electrochemical immunosensors in clinical immunoassays: carcinoembryonic antigen as a model," Biosensors and Bioelectronics (2010) p. 2379-2383, 25.
Zhou, J. Y. et al, "Novel in-Situ Decoration of Single-Walled Carbon Nanotube Transistors with Metal Nano particles," J Nanosci Nanotechnol (2010) 10, 3890-3894.
Zhou, M. et al. "Electrochemical Sensing and Biosensing Platform Based on Chemically Reduced Graphene Oxide," (2009) Analytical Chemistry 81, 5603.
Zhou et al., "The tunable electrical properties of graphene nanobridges," J Mater Chem C 2013, 1, 2548-2552.
Zhu, Y. et al., "Graphene and Graphene Oxide: Synthesis, Properties, and Applications," Adv. Mater (2010) 22, 3906-3924.
Zhan et al., "Graphene Field-Effect Transistor and Its Application for Electronic Sensing," Small, (Jul. 1, 2014), pp. n/a-n/a, XP055200050, ISSN: 1613-6810, DOI: 10.1002/smll.201400463 * paragraphs [3.4.2.2], [3.4.6], [4.2.3], [04.3].
Vaziri, "Fabrication and Characterization of Graphene Field Effect Transistors," (Jun. 30, 2011), XP055443794, Retrieved from the Internet: URL:http://www.diva-portal.org/smash/get/d iva2:447154/FULLTEXT01.pdf [retrieved on Jan. 24, 2018] * paragraph [0003].
EP15827017.3 Extended European Search Report dated Feb. 1, 2018 (8 pages).
Chinese Patent Office Action for Application No. 201580053445.9 dated Sep. 17, 2018 (33 pages, English translation included).
Chang et al., "Mechanism of the effects of low temperature Al2O3 passivation on graphene field effect transistors," Carbon (2013) 53, 182-187.
Chang et al., ""Single-walled carbon nanotube field-effect transistors with graphene oxide passivation for fast, sensitive, and selective protein detection,"" Biosensors and Bioelectronics (2013) 42, 186-192.

\* cited by examiner

Sensitivity comparison

| Concentration / Sensitivity / Solvent | 1 nM | 10 nM | 100 nM | 1 µM |
|---|---|---|---|---|
| In DI water | 0.76% | 4.27% | 1.93% | 1.45% |
| In tap water | 0.82% | 3.57% | 1.46% | 1.58% |

REAL-TIME DETECTION OF WATER CONTAMINANTS

CROSS-REFERENCE TO RELATED APPLICATIONS

This application is a national stage filing under 35 U.S.C. 371 of international Application No. PCT/US2013/060859, filed Sep. 20, 2013, and claims the benefit of U.S. Provisional Patent Application No. 62/032,280, filed on Aug. 1, 2014, the entire contents of which are hereby incorporated by reference in their entireties.

STATEMENT REGARDING FEDERAL FUNDING

This invention was made with government support under grant number 0968887 awarded by the National Science Foundation. The government has certain rights in the invention.

BACKGROUND

Access to clean water is one of the grand challenges for engineering. Mercury and its compounds are among major aqueous contaminants due to their high toxicity and risk to human health. Even a trace amount of mercury intake can lead to acute or chronic damage to human body. Moreover, mercury and its derivatives also cause detrimental effects to ecosystem. Therefore, it is important to develop methods to efficiently and effectively detect their presence in water systems, especially at innocuous levels. Many other contaminants present challenges to access to clean water.

In general, FET-based biosensors are devices that respond to changes in its' biological environment and converts this response into a signal that can be read. FET-based biosensors have been used to detect biomolecules, such as DNA and single-bacterium, and biological conditions, such as pH. The detection of water contaminants in a sample provides valuable information for research and commercial applications, such as monitoring of environmental contamination or water supply systems.

SUMMARY

In one embodiment, the invention provides a field-effect transistor sensor for detecting a target in an aqueous environment comprising: a reduced graphene oxide layer coated with a passivation layer; one or more gold nanoparticles in contact with the passivation layer; and at least one probe bound to the one or more nanoparticles; wherein the nanoparticles are discrete nanoparticles.

In another embodiment, the invention provides a method for maintaining electronic stability in a field-effect transistor based water sensor comprising coating a reduced graphene oxide layer with aluminum oxide layer, wherein the aluminum oxide layer is about 1 to about 5 nanometers thick.

In a further embodiment, the invention provides a method for detecting a target in an aqueous sample comprising: contacting an aqueous sample with a sensor according to the present invention; applying a current to the sensor; and detecting a change in an electrical characteristic.

Other aspects of the invention will become apparent by consideration of the detailed description and accompanying drawings.

DETAILED DESCRIPTION

Figure 1:
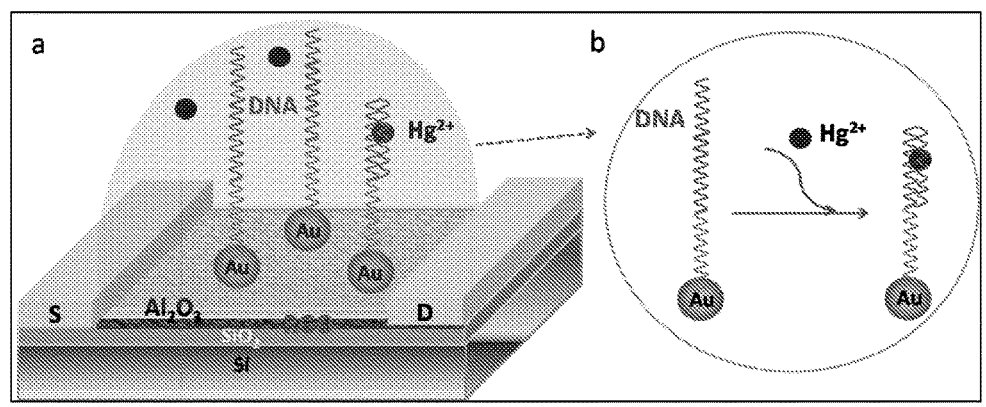
FIGS. 1A-B show a schematic of the FET-based biosensor.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein Electrical detection of biomolecules using nanomaterials can often achieve high sensitivity because nanomaterials are extremely sensitive to electronic perturbations in the surrounding environment. Carbon nanotubes (CNTs) and CNT-based field-effect transistor (FETs) biosensors have been used for the detection of protein binding and DNA hybridization events. Although CNT-based FETs are promising candidates for biosensors with high sensitivity, the device sensitivity is still limited by surface area and electrical properties of CNTs. CNTs as produced consist of both semiconducting and metallic tubes and there are no available methods for producing pure semiconducting or metallic tubes. The variations in the tube properties lead to devices with varying characteristics and performance, which is an obstacle to CNT-based FET reliability.

Graphene, a single layer of carbon atoms in a two-dimensional honeycomb lattice, has potential applications in the electrical detection of biological species due to their unique physical properties. Graphene-based sheets are flat and large in lateral dimensions, which make it easier for device fabrication (e.g., making electrical contact with electrodes). Compared to CNTs, graphene-based sheets have a higher carrier mobility and specific surface area, which enhances the sensor performance. The use of graphene has been explored for various applications. For example, large-sized graphene film FETs were fabricated for the electrical detection of DNA hybridization; graphene oxide (GO) was used in single-bacterium and label-free DNA sensors, and electrolyte-gated graphene FETs was used for electrical detection of pH. Despite the sparse demonstration of graphene for biosensing applications, graphene-based FETs have not been reported for detection of protein binding (e.g., antibody to antigen) events. Methods of directly immobilizing proteins onto CNTs or graphene oxide have been shown to be unstable and the attached proteins can be readily removed through simple washing processes that are frequently used during the biosensor fabrication. This introduces undesirable effects such as poor device reliability/repeatability and non-specificity of the sensor.

The present disclosure relates to a field-effect transistor (FET)-based biosensor and uses thereof, and in particular, to FET-based biosensors using graphene-based sheets decorated with nanoparticle-probe conjugates. The disclosed reduced GO (rGO) sheet FET-based biosensor proves to be surprisingly excellent at detecting contaminants, despite the fact that the electronic properties of reduced GO are not as good as those of pure graphene.

The present disclosure further provides a reliable method to detect water contaminants in real-time. In one embodiment, the present invention provides a method to immobilize probes in graphene-based biosensors and a methodology for avoiding nonspecific probe immobilization on graphene-based sheets and providing at the same time a stable binding for probes through robust nanoparticles. The immobilization of the probes via the nanoparticles allows for a more stable attachment of the probes to the nanostructure. The more stable attachment provides improved device reliability/repeatability and improved specificity of the sensor.

In an aspect, the present disclosure provides a field-effect transistor sensor comprising a reduced graphene-oxide layer coated with a passivation layer; gold nanoparticles in contact with the passivation layer; and probes bound to the gold nanoparticles.

In an aspect, the present invention provides an rGO FET-based sensor with $Hg^{2+}$-dependent DNA as a probe. An $Al_2O_3$ layer on rGO may be employed to separate analytes from conducting channel materials. The device shows good electronic stability, excellent lower detection limit (e.g. about 1 nM), and high sensitivity for real-time detection of $Hg^{2+}$ in an underwater environment.

In some embodiments, the passivation layer may include aluminum, zinc, titanium, silicon, or an oxide or nitride thereof, or a synthetic resin such as, but are not limited to, polymethyl methacrylate, polyester, polystyrene, polyethylene terephthalate, polycarbonate, polyvinylidene chloride or triacetate. For example, the passivation layer may comprise aluminum oxide. Suitably, the passivation layer is about 1 to about 5 nanometers thick. In certain embodiments, the passivation layer is about 3 nanometers thick.

With ultra-thin 1 nm $Al_2O_3$ deposition, the device may be only covered by discontinuous $Al_2O_3$ islands. In that case, the 1 nm $Al_2O_3$ layer could only be functional to passivate the rGO surface, but not fully protect rGO from the adsorption of free metal ions. Therefore, 1 nm thick layer deposition may lead to a lower sensitivity. It is possible that sensor performance could be further enhanced according to the practical need by simply depositing $Al_2O_3$ passivation layers with varying thicknesses and controlling the uniformity of passivation films. For example, better lower detection limits could potentially be achieved by adjusting the thickness of $Al_2O_3$ properly to enhance the gate electrical effect on the sensor device.

In some embodiments, the nanoparticles are discrete nanoparticles, that is, the areal density of the nanoparticles is less than a monolayer. The nanoparticles may be uniformly distributed on the sensor. Suitably, the nanoparticles are sufficiently far apart so that there is no electronic communication between the nanoparticles. In some embodiments the nanoparticles may be about 3 to about 5 nanometers in size. In some embodiments, the nanoparticles have an interparticle spacing of about 5 to about 10 nanometers. Suitably, the nanoparticles may have an interparticle spacing of about 8 nanometers.

The disclosed FET-based sensors may contain more than one probe. In some embodiments, the disclosed FET-based sensor may contain multiple probes which allow for detection of more than one target in a single sample. For example, multiple electrode pairs may be deposited onto one sensor chip, rGO and $Al_2O_3$ may be deposited on each of the electrode pairs, and each electrode pair labeled with a probe.

In some embodiments, each electrode pair has its own signal acquisition channel. When water passes the sensor surface, if one of the electrode pair shows signals, the corresponding contaminant could be determined. If multiple electrode pairs show signals, there are multiple contaminants in the water.

In some embodiments, a probe conjugated to the nanoparticle may include a protein, nucleic acid molecule, microorganism, and a low molecular weight organic compound. Examples include, but are not limited to, thioglycolic acid (TGA), glutathione (GSH), cysteine (Cys), dithiothreitol (DTT), 5-[1,2]dithi 5-[1,2]dithiolan-3-yl-pentanoic acid [2-(4-amino-phenyl)ethyl]amide (DPAA), ferritin, and a tin-organic receptor. One of ordinary skill in the art would be able to identify a suitable probe for a desired target.

The target may be of any origin, including natural, agricultural, water treatment process, human- or animal-caused, or microbiological (e.g., viral, prokaryotic, and eukaryotic organisms, including bacterial, protozoal, and fungal, etc.) depending on the particular purpose of the test. In some embodiments, the target is a water contaminant regulated by the Environmental Protection Agency, see, e.g. those listed at water.epa.gov. In some embodiments, the target may be a cation, such as Pb and Hg ions. In some embodiments, the target may be an anion, such as fluoride, phosphates, chlorides, or nitrates. In some embodiments, the target may be a metal, e.g., a heavy metal, such as lead, arsenic, cadmium, copper, iron, or mercury. In some embodiments, the target may a microorganism, such as bacteria, e.g. *Escherichia coli, Cryptosporidium, Giardia* sp., or *Legionella* sp., a virus, or other fungi. In some embodiments, the target may be an organic water contaminant, such as benzene and endrin. In some embodiments, the target may be an ion such that the pH of the sample may be determined. In some embodiments, the target may be a radionuclide, such as radium (e.g. radium 226 or radium 228) and uranium. In some embodiments, the target may be a water additive, such as a disinfectant or disinfectant byproduct, or fluoride. In some embodiments, the target may be a disinfectant, e.g. chlorine, chloramines, or chlorine dioxide, or a disinfectant byproduct, e.g. bromate, chlorite, haloacetic acids, or trihalomethanes.

For example, if bacteria, such as *E. coli*, is a target, the probe may be an antibody designed to bind the bacteria. If lead is a target, the probe may be GSH or DNAzyme. If mercury is a target, the probe may be thioglycolic acid (TGA). If arsenic is the target, the probe may be DTT. If cadmium is a target, the probe may be cysteine (Cys). If a phosphate is the target, the probe may be ferritin. If a chloride is a target, the probe may be a tin-organic receptor. If the target is a nitrate, the probe may be 5-[1,2]dithi 5-[1,2]dithiolan-3-yl-pentanoic acid [2-(4-amino-phenyl)ethyl]amide (DPAA).

In one aspect, the present invention provides FET-based sensors with immobilized anti-*E. coli* antibodies which demonstrate real-time, label-free, step-wise, target-specific, and highly sensitive electrical detection of *E. coli* cells at concentrations as low as about 10 cfu/mL, and the sensitivity increases with increasing *E. coli* concentrations up to about $10^3$ cfu/mL. In an embodiment, mercury (II) ion concentration can be detected by the sensor as low as about $2.5 \times 10^{-8}$ M.

The U.S. Environmental Protection Agency (EPA) has set the maximum contaminant level for arsenic in drinking water as 0.010 mg/L, for mercury as 0.002 mg/L, for lead as 0.015 mg/L, and for cadmium as 0.005 mg/L. One of skill in the art would be able to determine the maximum contaminant level for a given contaminant, for example, at www.water.epa.gov.

The probe may be conjugated to the nanoparticle using methods known in the art. For example, stable gold nanoparticle protein conjugates can be prepared by passive adsorption due to electrostatic and hydrophobic interactions between the protein and the surface layer of the colloidal gold. Conjugation methods also include chemical complexing, which may be either ionic or non-ionic in nature, or covalent bonding. An example of chemical complexing method is disclosed in U.S. Pat. No. 5,521,289, which describes reducing a gold salt in an organic solvent containing a triarylphosphine or mercapto-alkyl derivative bearing a reactive substituent, X, to give small nanoparticles carrying X substituents on linkers bound to the surface through Au-P or Au-S bonds. The colloidal solution is treated with a protein bearing a substituent Y that reacts with X to link the protein covalently to the nanoparticle. An example of binding oligonucleotides to nanoparticles is disclosed in U.S. Pat. No. 7,208,587, which describes attaching oligonucleotides to nanoparticles by means of a linker comprising a cyclic disulfide. Biomolecules conjugated to nanoparticles are commercially available. Examples include gold nanoparticles labeled with anti-immunoglobulin G.

In some embodiments, the nanoparticle-probe conjugate is decorated onto the nanostructure using an electrospray and electrostatic force directed assembly method or a drop-casting method. An example of an electrospray and electrostatic force directed assembly method is disclosed in Mao et al., Nanotechnology (2008) 19:455610, which describes decorating carbon nanotubes with nanocrystals using a combination of an electrospray technique, which creates a high level of electrical charge on the electrosprayed aerosol nanocrystals, with directed assembly using an electrostatic field. In a drop-casting method, a nanoparticle-probe conjugate solution is dropped onto the nanostructure and allowed to dry. Various factors and conditions may influence the drop-cast procedure such as the liquid amount, liquid viscosity, liquid evaporation rates, drop height, drop angle, drop atmosphere, drop splash, the dropping device and the desired depth or height, width, configuration and other dimensions of the nanostructure to be decorated.

Using these non-chemical methods, the nanoparticle, and hence the nanoparticle-probe conjugate, is attached to the nanostructure using non-covalent bonding, such as hydrogen bonds, electrostatic bonds, van der Waals forces, and hydrophobic bonds. The nanoparticles and hence the nanoparticle-probe conjugates may be attached to the nanostructure by van der Waals forces. The non-covalent attachment of the nanoparticle to the nanostructure avoids the effect of changing the electrical characteristics of the nanostructure or graphene-based sheet that may occur with a covalent bond, such as when wet-chemistry strategies are used to assemble nanoparticles onto nanostructures.

In some embodiments, the source and drain electrodes may be formed of any material having electrical conductivity. Examples include, but are not limited to, gold (Au), platinum (Pt) or palladium (Pd). In some embodiments, the substrate may include silicon, silicon dioxide, aluminum oxide, sapphire, germanium, gallium arsenide an alloy of silicon and germanium or indium phosphide. An example of a substrate includes a Si wafer.

The method of detecting a target in a sample includes contacting the FET-based biosensor with a sample containing or suspected of containing the target and monitoring a change in an electrical characteristic. The method of detecting the target involves measuring an electrical signal generated by the conversion of the interaction between the target and the probe of the sensor into corresponding output information and/or signals.

After the introduction of target, the target interacts with the probe of the nanoparticle-probe conjugate and induces significant changes in the electrical characteristics of the FET-based biosensor device, which would be investigated by FET and direct current (dc) measurements. In some embodiments, the change in an electrical characteristic as a function of time indicates the presence of the target. In some embodiments, the electrical characteristic may include conductance, capacitance, potential, resistance and inductance.

Suitably, there is a linear relationship between Ra and Ra-Ri (Ra: device resistance before dropping; Ra-Ri: device resistance change). In one example, an FET-based sensor according to the present invention showed a very uniform dynamic curve for detection of Pb ions with a detection limit of about 0.1 nM. For ions, such as Pb and Hg, the detection limit is as low as about 1 nM. For bacteria, such as E. coli, the detection limit is as low as about 1 cfu/mL.

In some embodiments, the binding event between the target and the probe would induce an increase in the electrical signal. In some embodiments, the electrical signal would increase at least 0.001%, 0.01%, 0.1%, 1%, 10%, 20%, 50%, 70% or more, compared to the electrical signal before the sample was added to the FET-based biosensor or compared to the electrical signal of a control sample. For example, an increase in resistance indicates the presence of a target in the sample.

In some embodiments, the binding event between the probe and the target would induce a decrease in the electrical signal. In some embodiments, the electrical signal would decrease at least 0.001%, 0.01%, 0.1%, 1%, 10%, 20%, 50%, 70% or more, compared to the electrical signal before the sample was added to the FET-based biosensor or compared to the electrical signal of a control sample. A control sample may include a similar composition to the tested sample but without any target or alternatively, may contain a known quantity of the target.

Without wishing to be bound by theory, it is believed that sensing signal from the hybrid structure of rGO decorated with recognition-group-functionalized Au NPs is based on the fact that channel conductance changes sensitively due to either electron donating or withdrawing effect of target ions. A specific recognition group (or a probe) is anchored to the rGO surface through Au NPs and further used to immobilize target ions. Due to the work function difference between Au NPs (5.1-5.47 eV) and reduced graphene oxide (4.2 eV), electrons may transfer between the rGO and the Au NPs and thereby change the drain current. The adsorption of target ions onto probes may lead to a carrier concentration change in rGO due to the effective electronic transfer between the rGO and Au NPs. The electrical detection of target agent that binds to probes may be accomplished by measuring the change in the electrical characteristics of the device.

The change in the electrical characteristic may be transmitted to a display. That display may be on a unit comprising the sensor, or it may be on a smartphone or other handheld device. In some embodiment, the display may be remote and the change in electrical characteristic may be transmitted wirelessly to the display. For example, the disclosed FET-based sensors may be present in a residential water supply system and the change in electrical characteristic may be transmitted via the existing wireless networks used for the water meter.

The disclosed FET-based biosensors are suitable for home or industrial use. For example, the disclosed FET-based sensors may be used to analyze a waste-water treatment process, to optimize chemical usage for water treatment, or to analyze water additives, such as fluorine or chlorine. In some embodiments, the disclosed FET-based sensors may be used in the water distribution system to monitor the water supply.

The invention is further described in the following non-limiting examples.

EXAMPLES

Example 1

Synthesis of FET-Based Sensors

Materials. Graphene oxide (GO) was ordered from ACS MATERIAL, which was synthesized by using the modified Hummer's method. 2-aminoethanethiol (AET) and glutaraldehyde (GA) were purchased from Sigma-Aldrich. Tween 20 and cold water fish gelatin were ordered from Tedpella. Anti-*E. coli* O157:H7 antibodies and *E. coli* O157:H7 cells were purchased from KPL, Inc. Phosphate buffered saline (PBS) (pH 7.4, ×1) (Fisher BioReagents) was used as the solvent for anti-*E.coli* O157:H7 antibodies. All solutions were prepared with deionized (DI) water (Cellgro). Cell culture grade water was purchased from Mediatech, Inc.

Device fabrication. Thermally-reduced monolayer graphene oxide (TRMGO) FETs were fabricated by self-assembly of GO sheets on the AET-modified Au interdigitated electrodes with both finger-width and inter-finger spacing (source and drain separation) of about 2 μm and a thickness of 50 nm. The electrodes were fabricated using a photolithography process on a highly-doped Si wafer with a top layer of dry-formed $SiO_2$ (thickness of 200 nm). The prepared electrodes were immersed into AET (1 mg/mL) solution at a concentration of 10 mM for 10 min and a monolayer of AET was assembled on the electrodes. The modified device was immersed into a GO dispersion with the assistance of sonication (Bransonic 1510-DTH); without sonication, the multilayer or folded layers of GO will form on the electrodes. After 1 min, a monolayer of GO film was deposited on the electrodes due to electrostatic interactions. The device was next annealed in an argon flow (1 liter per minute) for 1 h at 400° C. to reduce oxygen-containing groups in order to improve the semiconducting property and to reduce the junction barriers between the Au electrodes and TRMGO. Isolated Au nanoparticles (NPs) as scaffolds for immobilizing special probes were deposited on the TRMGO using an RF (60 Hz) Emitech K550x Sputter coater apparatus with an Au target (99.999% purity) at an Ar pressure of 0.03 mbar. The deposition time was 2 s with a working current of 10 mA.

Immobilization. The prepared device was immersed into an AET (1 mg/mL) solution with a concentration of 10 mM for 1 h. After being thoroughly rinsed with DI water and dried under a stream of nitrogen gas, the modified device was treated by a 25% GA solution at 25° C. for 1 h. After that, the device was incubated in the PBS containing anti-*E. coli* 0157 (10 μg/mL) antibodies at 4° C. for 12 h. Finally, the device was incubated with a blocking buffer (0.1% tween 20) for 2 h at room temperature and then washed with the cell culture water.

Characterization. Electrical measurements were performed on TRMGO sensors using a Keithley 4200 semiconductor characterization system at room temperature. The sensing signal of the device was recorded by monitoring the change in the drain current (ISD) for a given source-drain voltage (VSD) when the device was exposed to different concentrations of target materials.

Figure 2:
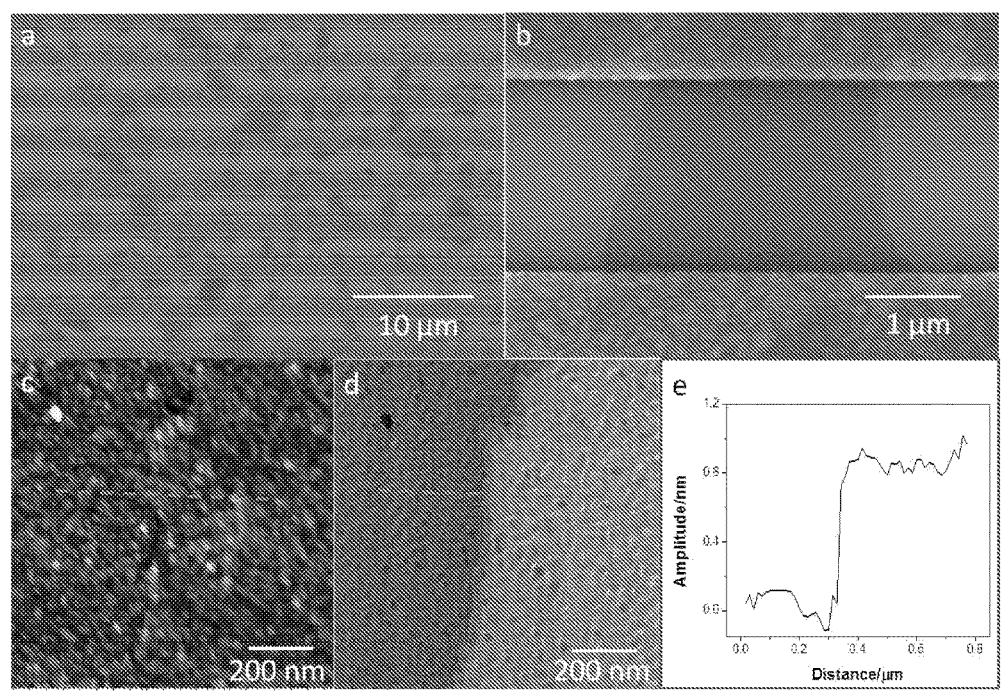
FIGS. 2A-E show in (A) and (B) SEM images of TRMGO sheets across the electrode gaps. AFM data (tapping mode) of TRMGO on the silicon wafer; (C) height and (d=D) phase images of the same zone at a cross-sectional area. The dashed line indicates a scanning trace of the TRMGO. (E) Height profile of TRMGO obtained by scanning from bare silicon wafer to TRMGO.

To inspect topographies of self-assembled TRMGO sheets on the electrodes, scanning electron microscopy (SEM) and atomic force microscopy (AFM) were employed. FIG. 2A shows SEM images of TRMGO distribution on Au electrodes. The lateral dimensions of TRMGO sheets typically ranged from several hundred nanometers to several micrometers on the devices with largest TRMGO sheets exceeding 3 μm (FIG. 2A). The area density of TRMGO sheets across electrodes was evaluated as approximately 5 sheets per 10 $\mu m^2$, which confirms that TRMGO sheets were uniformly distributed on the modified electrodes.

FIG. 2B shows an individual transparent TRMGO sheet on the electrodes, which indicates the GO sheet is comfortably positioned across the gap between the electrodes. FIG. 2C and FIG. 2C show an AFM image of a TRMGO sheet on the device. The thickness of the sheet measured through the cross-sectional height profiles from AFM data is 0.8-0.9 nm, which is consistent with monolayer TRMGO sheets. Both SEM and AFM images show that GO monolayers are morphologically stable with respect to the thermal reduction process.

Figure 3:
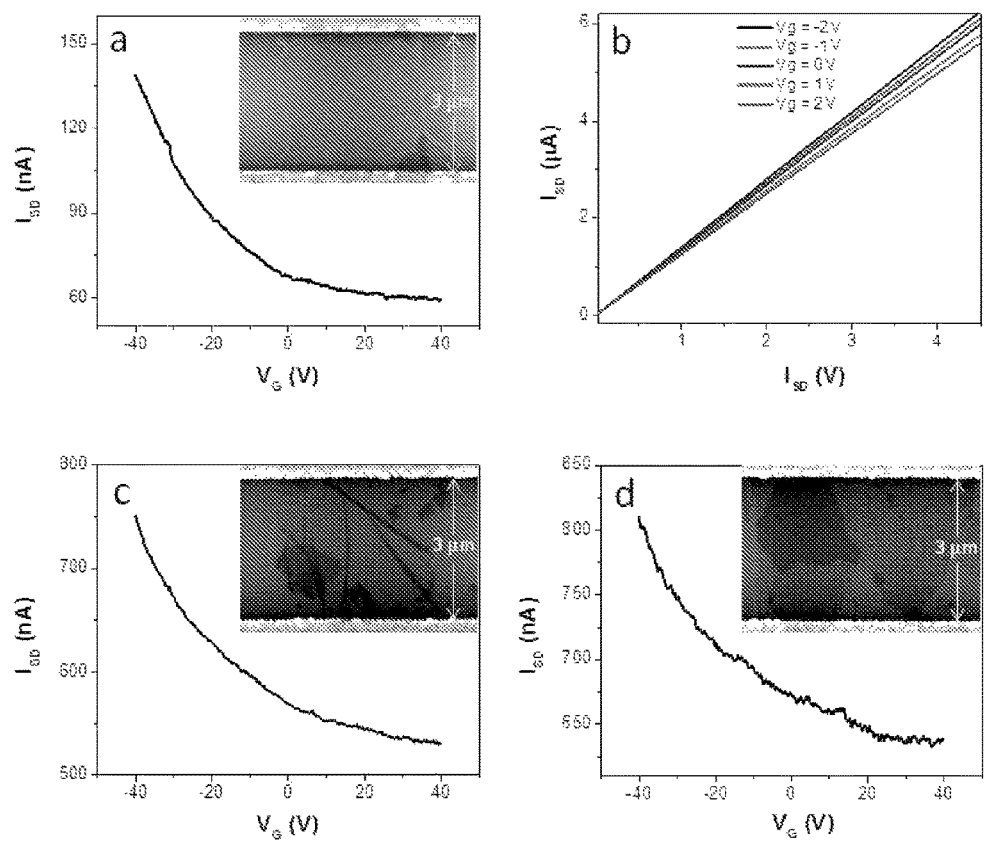
FIG. 3A-D show in (A) The FET I-V curve of TRMGO on SiO2/Si substrate (ISD=100 mV). Inset shows an SEM image of a monolayer GO sheet bridging the electrode gap. (B) ISD-VSD output characteristics of the TRMGO FET device at different bottom-gate VG from −2 to 2 V with an interval of 1 V. (C) The FET I-V curve of the crumpled GO FET device. Inset shows an SEM image of a crumpled GO across the electrode gap. (D) The FET I-V curve of the multilayer GO FET device. Inset shows an SEM image of multilayer GO sheets across the electrode gap.

For FET sensors, the field effect responses of TRMGO devices should be rapid and sensitive. To investigate the electrical properties of TRMGO FET devices, measurements were carried out in air at room temperature using the back-gated FET devices. FIG. 3A shows the typical $I_{SD}$-$V_G$ characteristics of a TRMGO FET device, in which $V_G$ is the gate voltage and $I_{SD}$ is the drain current. While the gate bias was varied from −40 to +40 V, the current of the device decreased from 139 to 59 nA. The decrease in conductivity with increasing voltage indicates the TRMGO sheets are p-type semiconducting materials. More importantly, the proposed TRMGO device shows good switching performance with an on/off current ratio of 2.35. This has been repeated with more than one hundred devices, which show similar electrical properties such as conductivity (~140 kΩ) and current on/off ratio (~2.3). Thus, the electrostatic self-assembly method with the assistance of ultrasonication can be used to form stable, uniform devices over a large area without aggregation.

To further examine the electrical characteristics of TRMGO FET devices, a bottom-gate voltage was applied on the devices from −2 to 2 V with an interval of 1 V. The drain-source current decreased with increasing gate voltage, as shown in FIG. 3B, which indicates the device response is sensitive to the gate voltage. Moreover, devices displayed an Ohmic-contact behavior, indicating the sensing mechanism in the TRMGO FET system is dominated by electrostatic gating. In the sonication fabrication process of the device, GO sheets deposited on the electrodes by the self-assembly method are monolayer and transparent, and the GO-based FET device shows good semiconducting properties. Without sonication, GO sheets deposited on the electrodes are likely to form folded or multilayer GO films (insets of FIGS. 3C and 3D), leading to devices with a lower on/off current ratio (1.41 and 1.27 for folded and multilayer GO, respectively). For FET biosensor applications, it is generally believed that the sensitivity has a strong dependence on the on/off current ratio of sensors, especially on the subthreshold slope.

Example 2

Detection of *E. Coli*.

Figure 4:
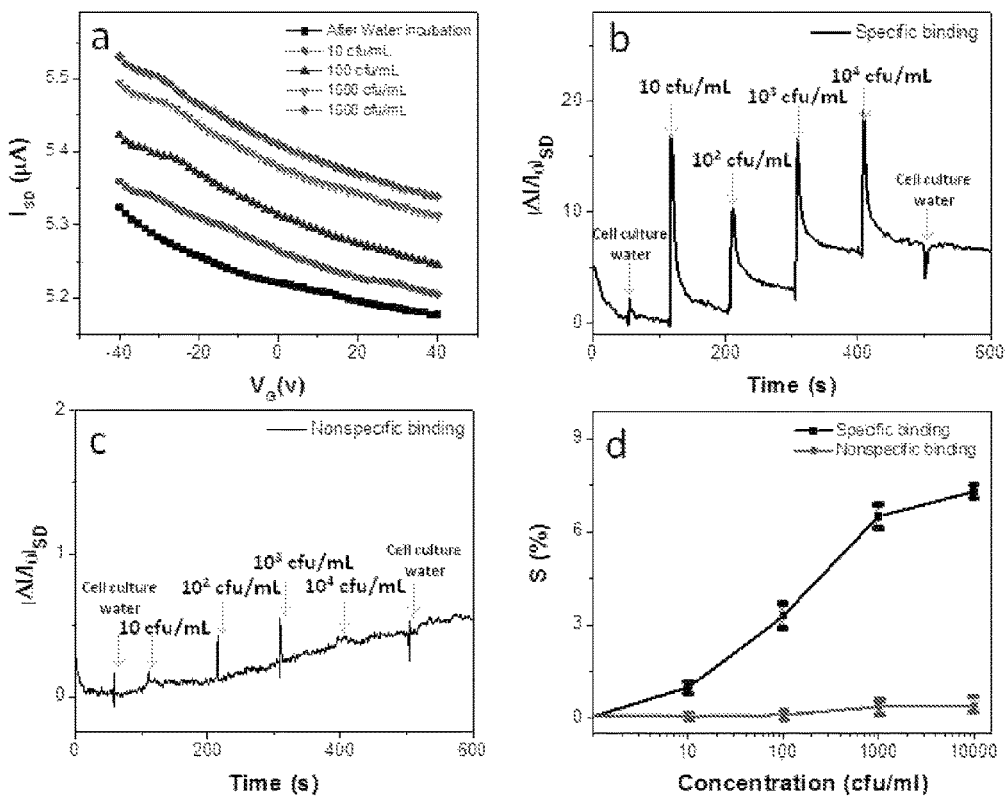
FIGS. 4A-D show in (A) Typical gate voltage dependence ($V_{SD}$=0.1 V) of $I_{SD}$ upon the introduction of E. coli cells of different concentrations. (B) Dynamic response of the devices exposed to different concentrations of E. coli cells for specific binding in the TRMGO FET device. (C) Non-specific binding in the TRMGO FET device (without anti-E. coli antibody probes). (D) The calibration curve of the TRMGO FET device (sensitivity S=$\Delta I/I_0$ vs. concentration). Error bars were obtained through multiple measurements.

The FET-based sensors prepared according to Example 1 were used to detect *E. Coli*. The sensing performance of TRMGO FET devices was investigated using anti-*E. coil* antibodies as probes. The device was exposed to various concentrations of *E. coli* cells in the cell culture grade water. The changes in transfer curves of the FET sensor after adding selected concentrations of *E. coli* cells (10, $10^2$, $10^3$, and $10^4$ cfu/mL) have been investigated. It can be observed that the conductance of the devices continued to increase with increasing concentrations of *E. coli* cells (FIG. 4A). As the TRMGO FET was operated in the p-type region ($V_G=0$ V), the device conductance increase is due to increased hole concentration, which is induced by the highly negatively charged bacterial wall and is in agreement with previous reports.

The dynamic response of TRMGO-based devices for detecting *E. coli* cells was measured with the specific binding as shown in FIG. 4B and non-specific binding as shown in FIG. 4C, respectively. The conductance of the device with specific binding increased correspondingly with the addition of *E. coli* cell solution, and the current change of the device was around 1.1% with the introduction of 10 cfu/mL. For comparison, a control experiment was carried out on a device without modification of anti-*E. coli* antibody probes. In contrast, controlled injection of *E. coli* cells had almost no effect on the conductance of the TRMGO devices without the presence of probes (FIG. 4C). Therefore, it is confirmed that the conductance increase is solely attributed to the specific binding between probes and target materials.

The sensor sensitivity (relative conductivity change, %) is presented as a function of *E. coli* cell concentration in FIG. 4D. The TRMGO device had a higher sensitivity for all *E. coli* cell concentrations than that of the device with non-specific binding. For specific binding, the sensitivity gradually increased linearly for *E. coli* cell concentrations from 10 cfu/mL to $10^3$ cfu/mL and the response amplitude depends on the *E. coli* cell concentration. If more *E. coli* cells bind to anti-*E. coli* antibodies on the devices, a larger gating effect will be introduced and more significant carrier concentration change will result, thereby leading to more conductivity change in the sensor. This sensing mechanism was also confirmed by transfer curves in a previous report; however, at a higher concentration of $10^4$ cfu/mL, the sensor signal was not directly proportional to the increased cell concentration because the sensor became saturated. This phenomenon indicates that most of the binding sites on the devices are occupied by target analytes at the $10^4$ cfu/mL concentration level. For non-specific binding (without anti-*E. coli* cell probes), the TRMGO device showed only a very weak response, because the blocking buffer can effectively block physical adsorption of *E. coli* cells on the device. Thus, the normalized sensitivity N can be written as $$N=c(1/k+c)^{-1}$$

where c and k represent the concentration of *E. coli* cells in the solution and the equilibrium constant between the *E. coli* cells and anti-*E. coli* antibodies, respectively. The sensor response can be expressed in a linear form to logarithmic concentration in a certain range of concentrations (10, $10^2$, and $10^3$ cfu/mL). By fitting the data in FIG. 4D using this equation, the equilibrium constants are estimated as $6.8\times10^4$ mL/cfu in specific binding and $1.3\times10^3$ mL/cfu in non-specific binding, respectively. The specific binding equilibrium constant is much higher, which means that the specific binding offers much more sensitive responses than non-specific binding for detection of *E. coli* bacteria.

Figure 5:
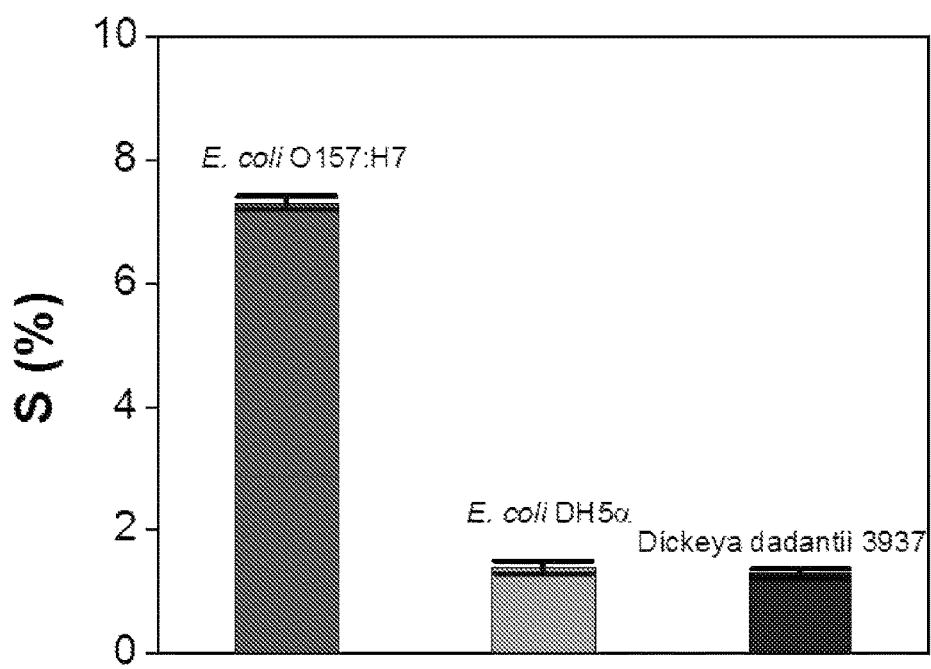
FIG. 5 shows a comparison of the sensor sensitivity in response to E. coli O157:H7 ($10^4$ cfu/mL), E. coli DH5α ($10^4$ cfu/mL), and Dickeya dadantii 3937 ($10^4$ cfu/mL). Error bars were obtained through multiple measurements.

To establish the sensor's specificity for *E. coli* cells, it was interrogated with the non-pathogenic *E. coli* strain DH5a ($10^4$ cfu/mL) and the plant-pathogenic bacterium *Dickeya dadantii* 3937 ($10^4$ cfu/mL) with the same procedure as that used for specific detection of the *E. coli* O157:H7 cells. The performance evaluation of the sensor's specificity has been summarized in FIG. 5. It indicates that the sensor sensitivity from the *E. coli* DH5α(1.4%) and *Dickeya dadantii* 3937 (1.3%) is significantly smaller than that from the *E. coli* O157:H7 (7.3%). This result further confirms that the sensor response is from the binding of *E. coli* cells to anti-*E. coli* antibodies and the target materials can be selectively detected by the TRMGO FET sensor.

Example 3

Detection of Hg(II) Ions

Materials. Graphite oxide was synthesized by the oxidative treatment of purified natural graphite (SP-1, Bay Carbon, Mich.) using a modified Hummers method. The graphite oxide was dissolved into water and centrifuged to remove possible agglomeration material. The graphite oxide was then fully exfoliated in water due to its strong hydrophilicity originated from the existence of oxygen functional groups. Individual graphene oxide (GO) sheets can be obtained from the stable suspension with the aid of ultrasonication.

Au NPs (5 nm colloidal gold) were purchased from BB international. TGA was purchased from Sigma Aldrich. Mercury (II), sodium (I), and calcium (II) ion solutions were prepared by adding chloride salts in DI water.

Device fabrication. The sensing device consisted of a 200 nm thermally-formed $SiO_2$ on Si substrates, where $SiO_2$ layer acted as the gate dielectric and Si as a back gate. Interdigitated electrodes with both finger-width and inter-finger spacing (source-drain separation) of about 1 μm were patterned using an e-beam lithography process followed by e-beam deposition of Cr/Au and lift-off To place GO sheets between interdigitated electrodes, one droplet of the GO suspension was pipetted onto the electrodes and dried under room temperature. Thermal reduction of GO was carried out in a tube furnace (Lindberg Blue, TF55035A-1) by heating for 1 hr at 300° C. in Ar flow (1 1 pm) to remove residue solvents, reduce graphene oxide, and improve the contact between the rGO sheet and electrodes. After heating, samples were quickly cooled to room temperature within ~5 min with the assistance of a blower. After the annealing process, rGO was found to be immobilized between interdigitated fingers even after several cycles of washing and drying, which was confirmed by SEM imaging. Au NPs were then assembled onto the surface of rGO sheets by a previously reported method, which combines electrospray with an electrostatic force directed assembly (ESFDA) technique. The Au NPs assembly time was around 2 hrs. To exclude solution-induced interference to the device, a standard e-beam lithography process was used to encapsulate the interdigitated electrodes regions with 400-nm thick 4% polymethyl methacrylate (PMMA), leaving only the sensing region (rGO coated with Au NPs) accessible for the liquid solutions. Briefly, PMMA solution was first spin coated onto the device. E-beam lithography was then used to pattern the PMMA layer such that the PMMA covering sensing region (between electrodes) could be removed, resulting in encapsulated electrodes and open sensing area. After that, the device was submerged in 10 mM TGA solution for 24 hrs at room temperature to functionalize Au NPs. The sensor device was then rinsed with DI water for several times to remove extra TGA.

Characterization. Transport and electrical measurements were performed on rGO/TGA-AuNP hybrid sensors using a Keithley 4200 semiconductor characterization system. Three-terminal FET measurements were employed for device transport characteristics only, and all other electrical tests were operated by two-terminal measurement with a floating gate. Electrical conductance of the rGO/TGA-AuNP hybrid sensor was measured by fixing the drain voltage ($V_{ds}$) and simultaneously recording the drain current ($I_{ds}$) when the device was exposed to different concentrations of target ion solutions. All the sensing data was repeated by 3-4 sensors, and their similar sensing responses further confirmed sensor repeatability. A Hitachi S4800 field-emission scanning electron microscope (SEM) was used to characterize the morphology of rGO sheets at a 2 kV acceleration voltage.

Figure 6:
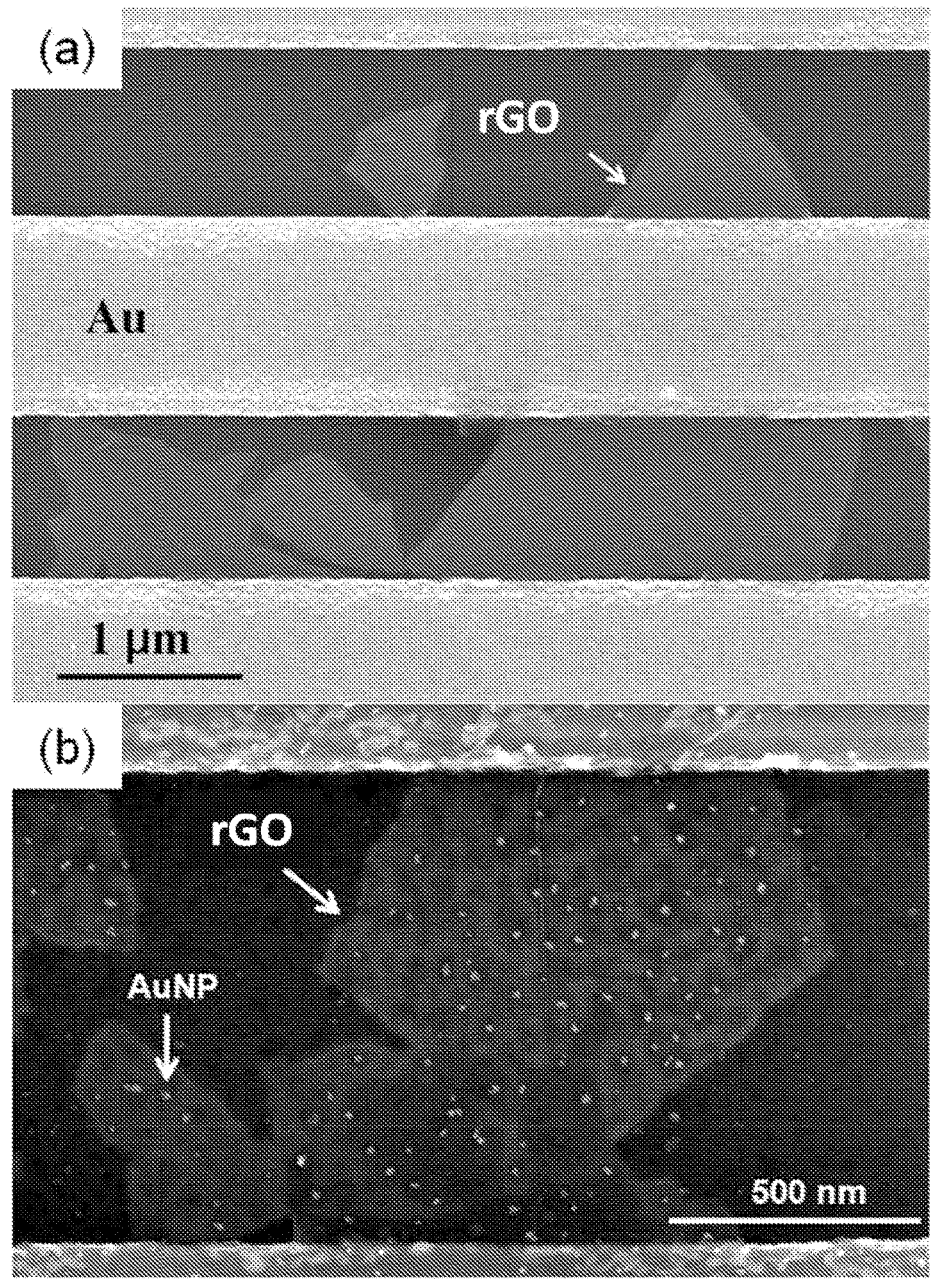
FIGS. 6A-B show SEM images of a GO sheet (A) and an rGO sheet decorated with TGA-AuNPs (B) spanning across interdigitated electrodes.

Results. FIG. 6A shows the SEM image of a single rGO sheet spanning across a pair of Au interdigitated electrodes. After the Au NP assembly, Au NPs were seen uniformly distributing on the surface of the rGO sheet without agglomeration (FIG. 6B). The van der Waals binding between Au NPs and rGO is strong enough to retain Au NPs in place even after several cycles of washing and drying.

TGA (HS—CH—COOH) has both a thiol (—C—SH) group and a carboxylic acid (—COON) group. The thiol group in TGA interacts with the surface of Au NPs, facilitating anchoring TGA on Au NPs. On the other hand, the carboxylic acid in TGA acts as a linker to immobilize the $Hg^{2-}$ ion because they can react to form R—COO—$(Hg^{2+})$—OOC—R chelates. Because of the strong bonding between gold and the thiol group, a self-assembled monolayer of TGA was formed on the gold surface, which was confirmed by X-ray photoelectron spectroscopy (XPS) and contact angle measurement.

Figure 7:
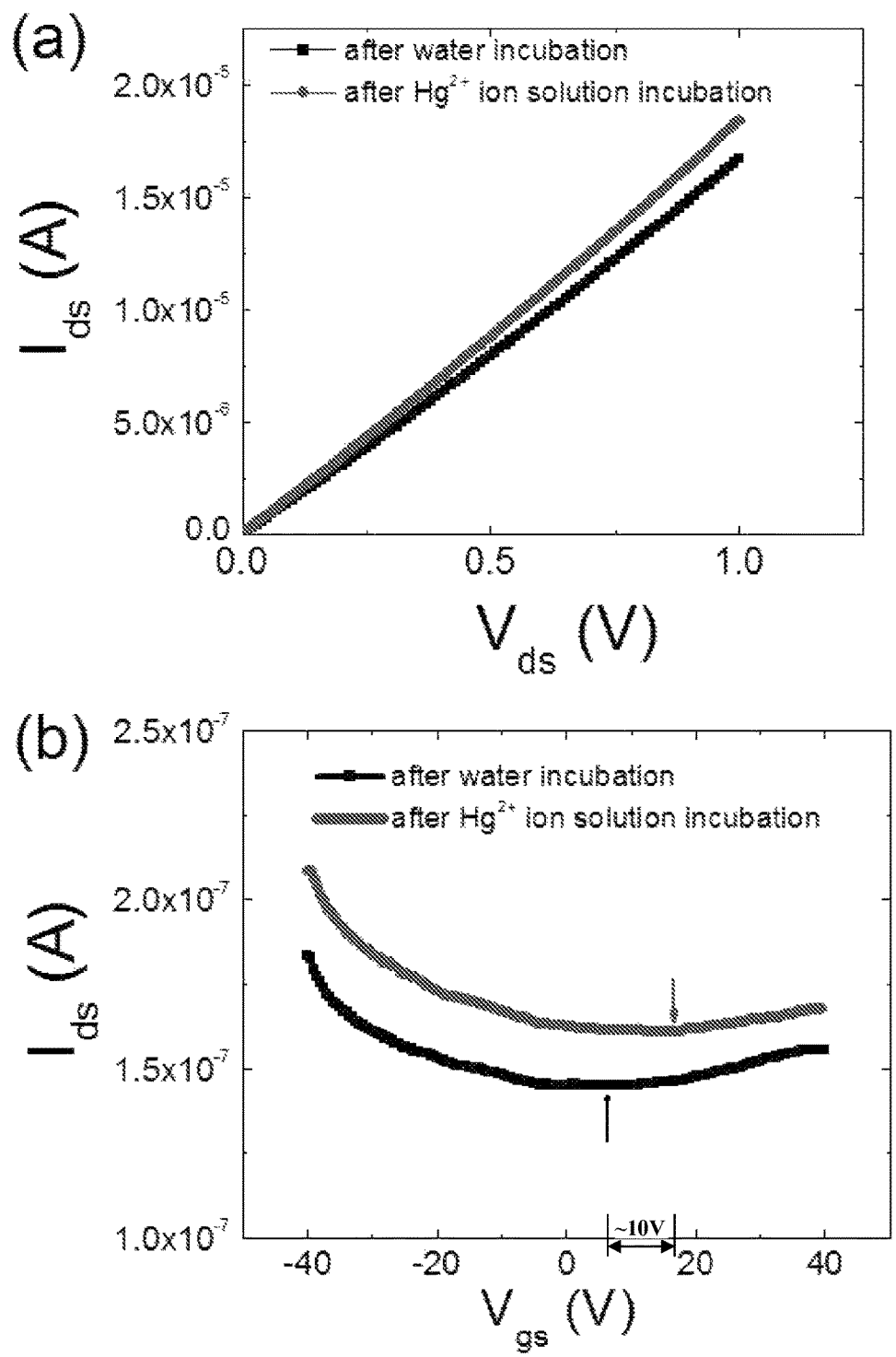
FIGS. 7A-B show $I_{ds}$-$V_{ds}$ (A) and $I_{ds}$-$V_{gs}$ (B) characteristics of an rGO/TGA-AuNP hybrid sensor exposed to water (black) and $10^{-5}$ M $Hg^{2+}$ ion (red) solutions (at 0.01 V drain voltage).

The drain current ($I_{ds}$) of the rGO/TGA-AuNP hybrid sensor as a function of the drain voltage ($V_{ds}$) or the gate voltage ($V_g$) was measured as the sensor was exposed to water and $10^{-5}$ M $Hg^{2+}$ ion solution, as shown in FIGS. 7A and 7B. The drain current increase for the rGO/TGA-AuNP hybrid sensor after exposure to $Hg^{2+}$ ion solution is due to the formation of R—COO—$(Hg^{2+})$—OOC—R chelates through reactions between $Hg^{2+}$ ions and the carboxylic acid groups of the TGA molecules on the Au NPs. The coupling of $Hg^{2+}$ ions with carboxylic acid groups can cause changes in the charge carrier concentration in rGO sheets. To counteract the accumulation of positive charges from $Hg^{2+}$ ions, electrons may transfer from the rGO to the Au NPs, increasing the hole concentration in the rGO and thereby increasing the drain current. Therefore, compared with water, exposure to $Hg^{2+}$ ion solution increased the conductance of the rGO/TGA-AuNP hybrid sensor. As shown in FIG. 7B, the Dirac point of the rGO/TGA-AuNP hybrid sensor shifted ~+10 V because of the immobilization of the $Hg^{2+}$ ions.

The gating effect was also reported as the possible sensing mechanism for positively charged antigen binding event because the accumulation of positively charged target analyte can act as positive potential gating and further reduce the electrical conductivity of the rGO. Based on the transport characteristic of the rGO/TGA-AuNP hybrid sensor, the transport through the rGO sheets is mainly dominated by positive charge carriers (holes) at floating gate ($V_{gs}=0$ V) condition. However, the electrical conductivity of rGO increased with the increase of the $Hg^{2+}$ ion concentration, showing the gating effect was negligible for our sensor platform. Further studies are required for additional understanding of the sensing mechanisms.

Figure 8:
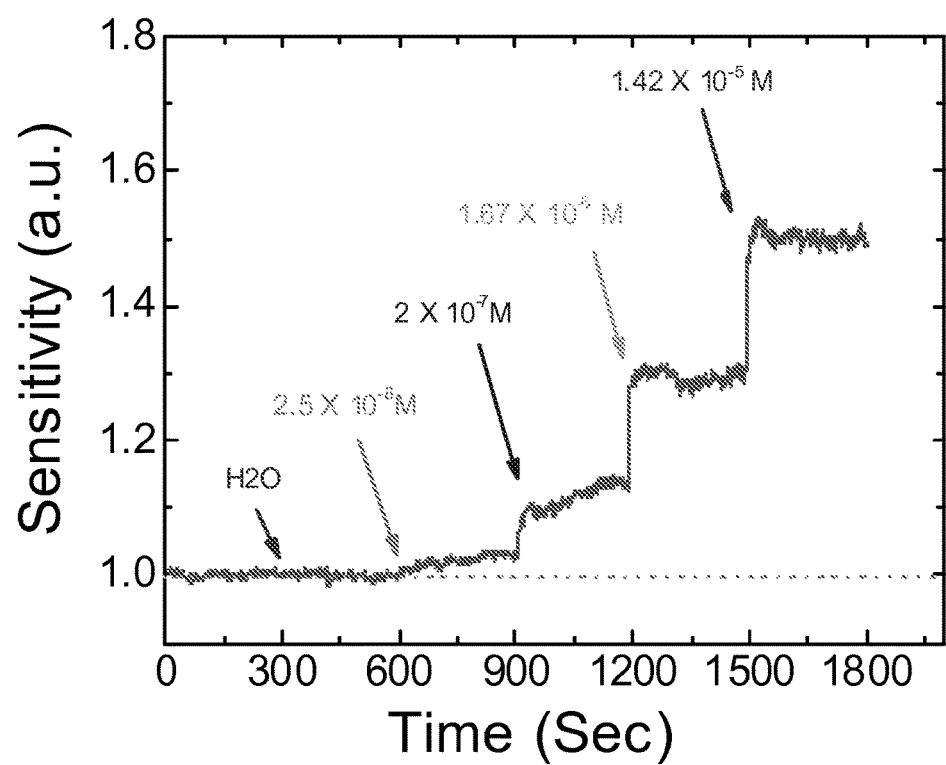
FIG. 8 shows the dynamic response (sensitivity versus time) of an rGO/TGA-AuNP hybrid sensor for $Hg^{2+}$ ion concentrations ranging from $2.5 \times 10^{-8}$ M to $1.42 \times 10^{-5}$ M.

FIG. 8 shows the dynamic response of an rGO/TGA-AuNP hybrid sensor with $Hg^{2+}$ ion concentrations ranging from $2.5 \times 10^{-8}$ to $1.42 \times 10^{-5}$ M. The drain current versus time was monitored and then sensitivity (defined as the source-drain current change ratio, or the ratio the sensor conductance in $Hg^{2+}$ solution to that in DI water) was obtained for different target $Hg^{2+}$ ion concentrations. There was no noticeable change observed upon the addition of DI water, implying the specificity and stability of the device. The sensor showed a rapid response when solutions with varying $Hg^{2+}$ concentrations were introduced to the device surface. The sensor responded within a few seconds for the $Hg^{2+}$ ions to diffuse through the liquid drop on the top of the device, in marked contrast to minutes or even hours required for conventional fluorescence sensors. The binding sites on the Au NPs were not fully occupied by $Hg^{2+}$ ions within a single testing and the sensitivity kept increasing with the addition of higher concentration $Hg^{2+}$ ions.

Three control experiments were performed to reveal the roles played by Au NPs and TGA probes in the hybrid sensing platform. The first control experiment was conducted using a bare rGO device without any Au NPs or TGA-functionalized Au NPs. The bare rGO device was insensitive to $Hg^{2+}$ ions. In the second control experiment, an rGO device was fabricated with the assembly of Au NPs, but without the TGA functionalization process. The rGO/AuNPs hybrid device was not responsive to the $Hg^{2+}$ ions either, implying that there was no obvious improvement in sensor sensitivity after the assembly of Au NPs. A third rGO device, which was processed with TGA modification but without the assembly of Au NPs, showed no sensitivity to the $Hg^{2+}$ ions. Without wishing to be bound by theory, this could be due to the lack of strong adhesion between TGA and rGO, which could lead to the removal of TGA from the rGO surface after washing with DI water. Therefore, these three control experiments suggest that the combination Au NPs and TGA modification of Au NPs is critical for rGO-based sensors to achieve good $Hg^{2+}$ sensing performance as shown in FIG. 8.

Figure 9:
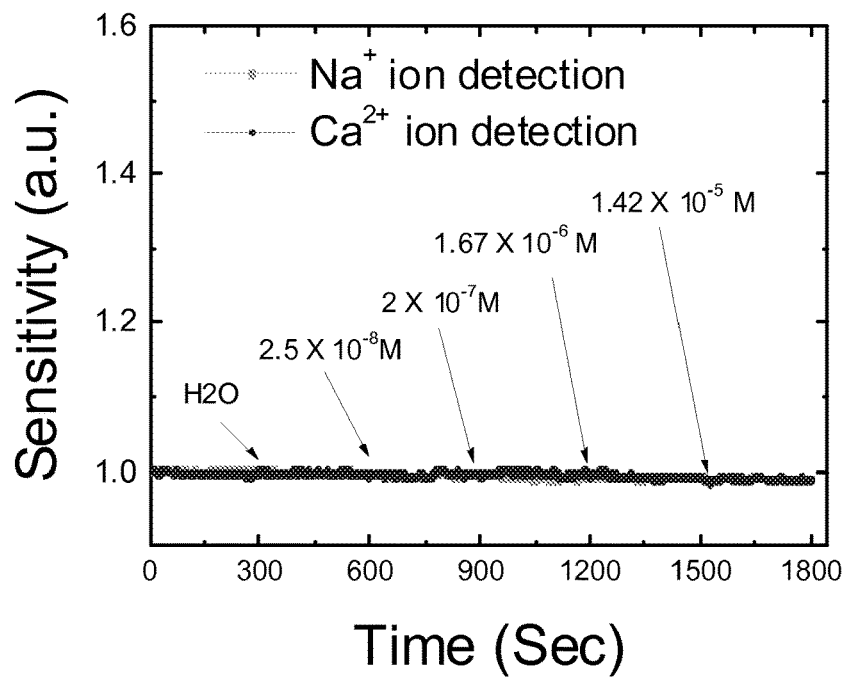
FIG. 9 shows an rGO/TGA-AuNP hybrid sensor showed no oblivious response to $Na^+$ and $Ca^{2+}$ concentrations ranging from $2.5 \times 10^{-8}$ M to $1.42 \times 10^{-5}$ M.

To demonstrate the specificity of the rGO/TGA-AuNP hybrid sensor, its sensing behavior was inspected when it was exposed to solutions containing interference species such as $Na^+$ and $Ca^{2+}$ ions. As the chelating effect of thiolate compound favors heavy metal ions such as $Hg^{2-}$, the interference of $Na^+$ and $Ca^{2+}$ ions was weak. The rGO/TGA-AuNP hybrid sensor indeed gave no obvious response upon the addition of $Na^+$ and $Ca^{2+}$ ions, as clearly shown in FIG. 9.

Figure 10:
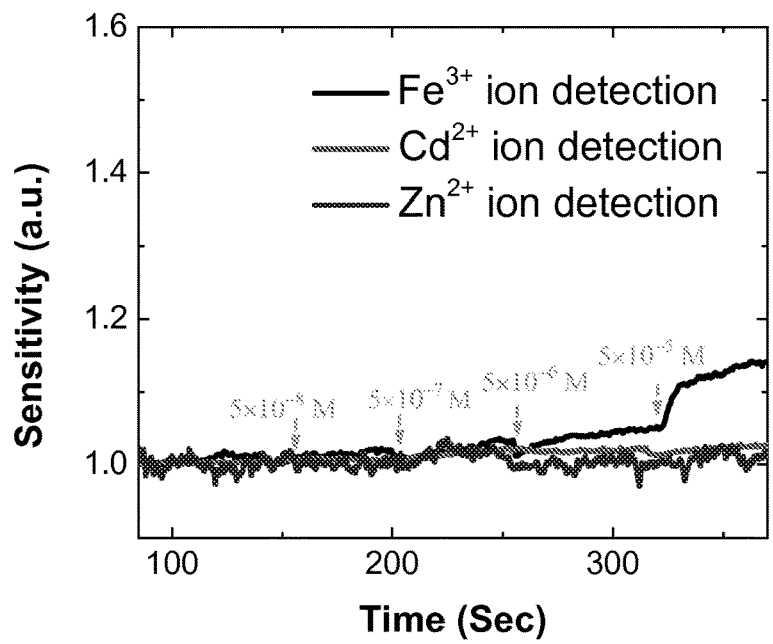
FIG. 10 shows the response to a variety of individual metal ions: $Zn^{2+}$, $Cd^{2+}$, and $Fe^{3+}$.
Figure 11:
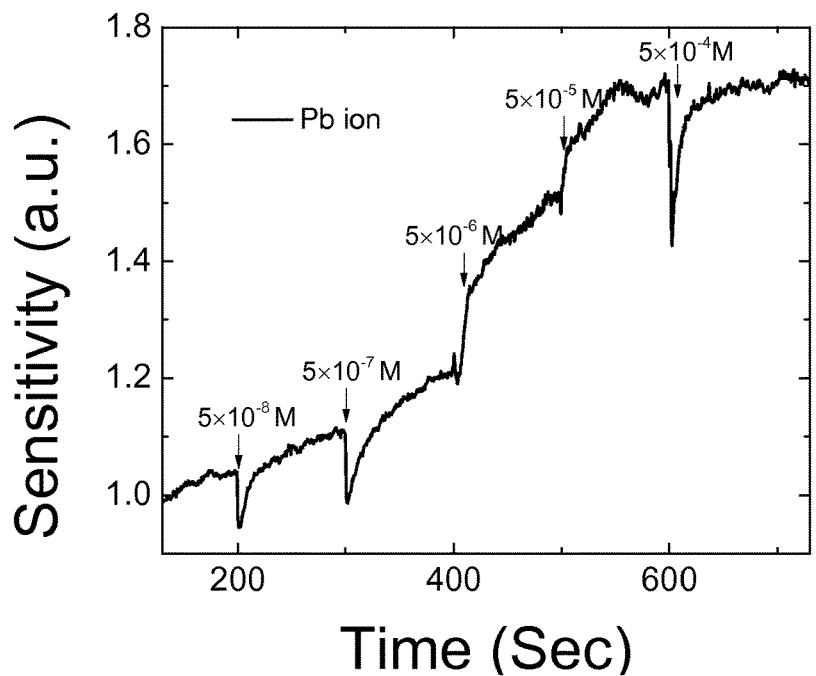
FIG. 11 shows the dynamic response (sensitivity versus time) of an rGO device with TGA modification for Pb2+.
Figure 12:
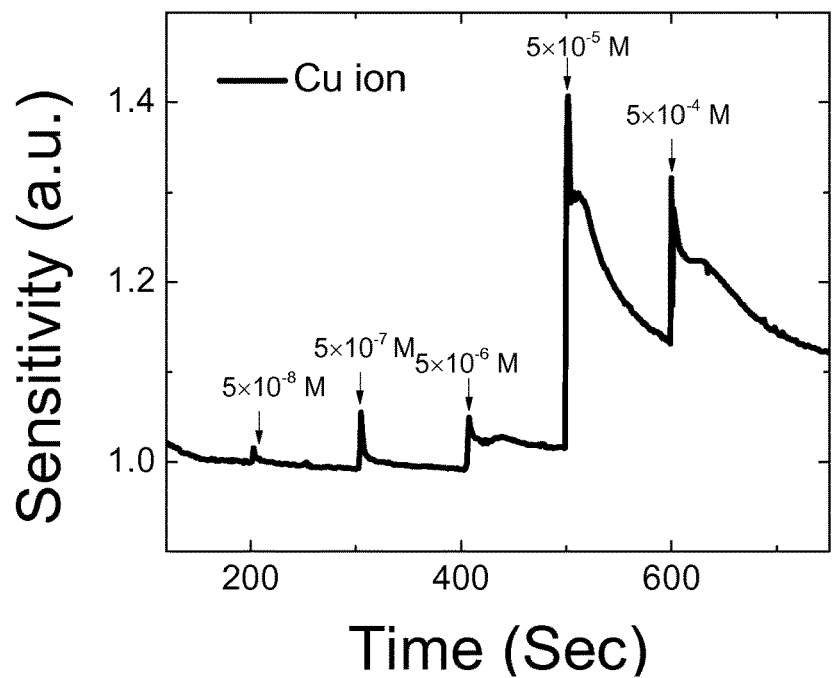
FIG. 12 shows the dynamic response (sensitivity versus time) of an rGO device with TGA modification for Cu2+.

To further confirm the sensor's specificity, a variety of other common heavy metal ions including $Zn^{2+}$, $Cd^{2+}$, and $Fe^{3-}$, have been investigated in FIG. 10. The $Zn^{2+}$ and $Cd^{2+}$ resulted in a very week response. But, for $Fe^{3-}$, the devices demonstrated a comparable sensitivity with $Hg^{2+}$, which maybe was attributed to the high affinity with carboxylic acid groups and more net positive charges of $Fe^{3+}$. The sensitivity limit of detection of $Fe^{3+}$ was about 5 μM, which was much lower than that of $Hg^{2+}$. For investigating selectivity with ions that are chemically more similar to $Hg^{2+}$, $Cu^{2+}$ and $Pb^{2+}$ have been examined (FIG. 11 and FIG. 12), which showed similar response with $Fe^{3+}$.

Example 4

Detection of Hg(II)

Materials. GO was ordered from ACS MATERIAL, which was synthesized by using the modified Hummer's method.28 2-aminoethanethiol (AET) was purchased from Sigma-Aldrich. All solutions were prepared with deionized (DI) water (Cellgro). DNA (5'-SH-TCA TGT TTG TTT GTT GGC CCCCCT TCT TTC TTA-3') was purchased from Integrated DNA Technologies (IDT). PBS (pH 7.4, ×1) (Fisher BioReagents) was used as the solvent for DNA.

Device formation. rGO FETs were fabricated by self-assembly of GO sheets on the AET-modified Au interdigitated electrodes with both finger-width and inter-finger spacing (source and drain separation) of about 2 μm and a thickness of 50 nm. The deposition process of GO sheets on the electrodes by the self-assembly method was performed as described in Example 1. The GO-deposited device was next annealed in an argon flow (1 liter per minute) for 1 h at 400° C. to reduce oxygen-containing groups in order to improve the semiconducting property.

$Al_2O_3$ passivation layers were deposited on the electrode by atomic layer deposition (ALD). Trimethylaluminum (TMA) and water were the two precursors for the binary reaction at 200° C. using 10 s diffusion time and 10 s interval between the two pulses. The thickness of the $Al_2O_3$ layer was controlled precisely by the deposition cycles with a deposition rate of 0.12 nm/cycle. Isolated Au nanoparticles (NPs) as scaffolds for immobilizing special probes were deposited on the $Al_2O_3$ using an RF (60 Hz) Emitech K550x Sputter coater apparatus with an Au target (99.999% purity) at an Ar pressure of 0.03 mbar.

Immobilization. A 10 µL aliquot of a 100 µM DNA (5'-SH-TCA TGT TTG TTT GTT GGC CCCCCT TCT TTC TTA-3') solution in ×1 PBS was injected onto Au NP-coated devices on top of the sensing area and the devices were incubated at room temperature for 90 min. Following DNA incubation, the devices were briefly rinsed with deionized water (DI).

Subsequently, the devices were exposed to solutions (Solvent: DI water) of each metal ion with different concentrations, as well as mixtures.

Characterization. Electrical measurements were performed on rGO sensors using a Keithley 4200 semiconductor characterization system at room temperature. The sensing signal of the device was recorded by monitoring the conductivity change for a given source-drain voltage (VSD) when the device was exposed to different concentrations of target materials. Scanning electron microscopy (SEM) was performed on a Hitachi S-4800. Raman spectroscopy was carried out by using a Renishaw 1000 B Raman microscope with a 632.8 nm HeNe laser with 3 accumulations of 10 seconds each.

Figure 13:
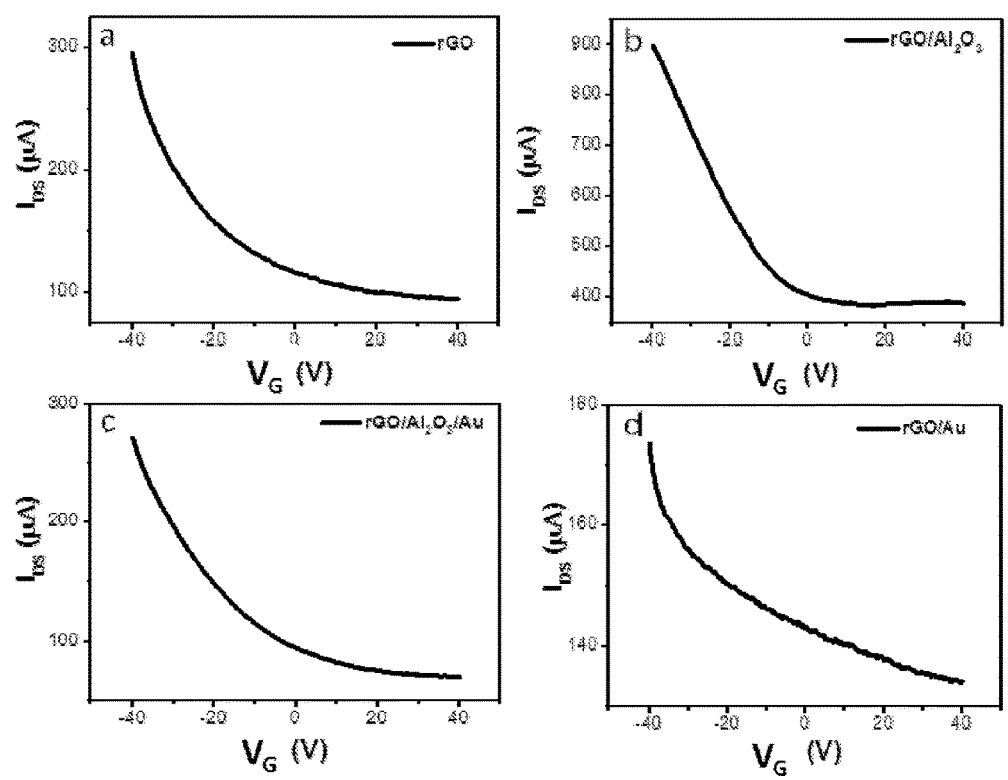
FIGS. 13A-D show FET curves of sensors on $SiO_2$/Si substrate ($I_{SD}$=100 mV): (A) bare rGO FET sensor; (B) rGO FET with an $Al_2O_3$ film coating; (C) rGO/$Al_2O_3$ with Au NP coating; (D) rGO/Au NP FET device without an $Al_2O_3$ film coating.

Results. To investigate the electrical properties of rGO/$Al_2O_3$/Au NP FET devices, outputs (drain-source voltage ($V_{DS}$)=0.1 V and gate-source voltage ($V_{GS}$) from −40V to 40 V) applied into back-gated FET devices under ambient conditions at room temperature. FIG. 13 shows the typical $I_{DS}$-$V_G$ characteristics of a bare rGO FET device. While the gate bias was increased from −40 to +40 V, the current of the device decreased from 297 to 94 nA, which indicates that the rGO sheets are p-type semiconducting materials as shown in FIG. 13A. More importantly, the rGO device shows good switching performance with an on/off current ratio of 3.15. After $Al_2O_3$ coating, the electrical conductivity is increased due to the enhancement of the field-effect mobility as shown in FIG. 13B, but the current on/off ratio (3.08) is similar to that of bare rGO devices. Subsequently, the $Al_2O_3$/rGO devices were coated by isolated Au NPs, whose electrical properties are similar to those of bare rGO devices as shown in FIG. 13C. Therefore, the incorporation of Au NPs does not significantly degrade the device performance with $Al_2O_3$ protection. In comparison, the electrical properties of rGO/Au NPs without $Al_2O_3$ coating were also measured (FIG. 13D), which showed a poor conductivity and a low current on/off ratio (1.29), due to a decrease in the hole mobility of rGO induced by the doping effect from Au NPs.

Figure 14:
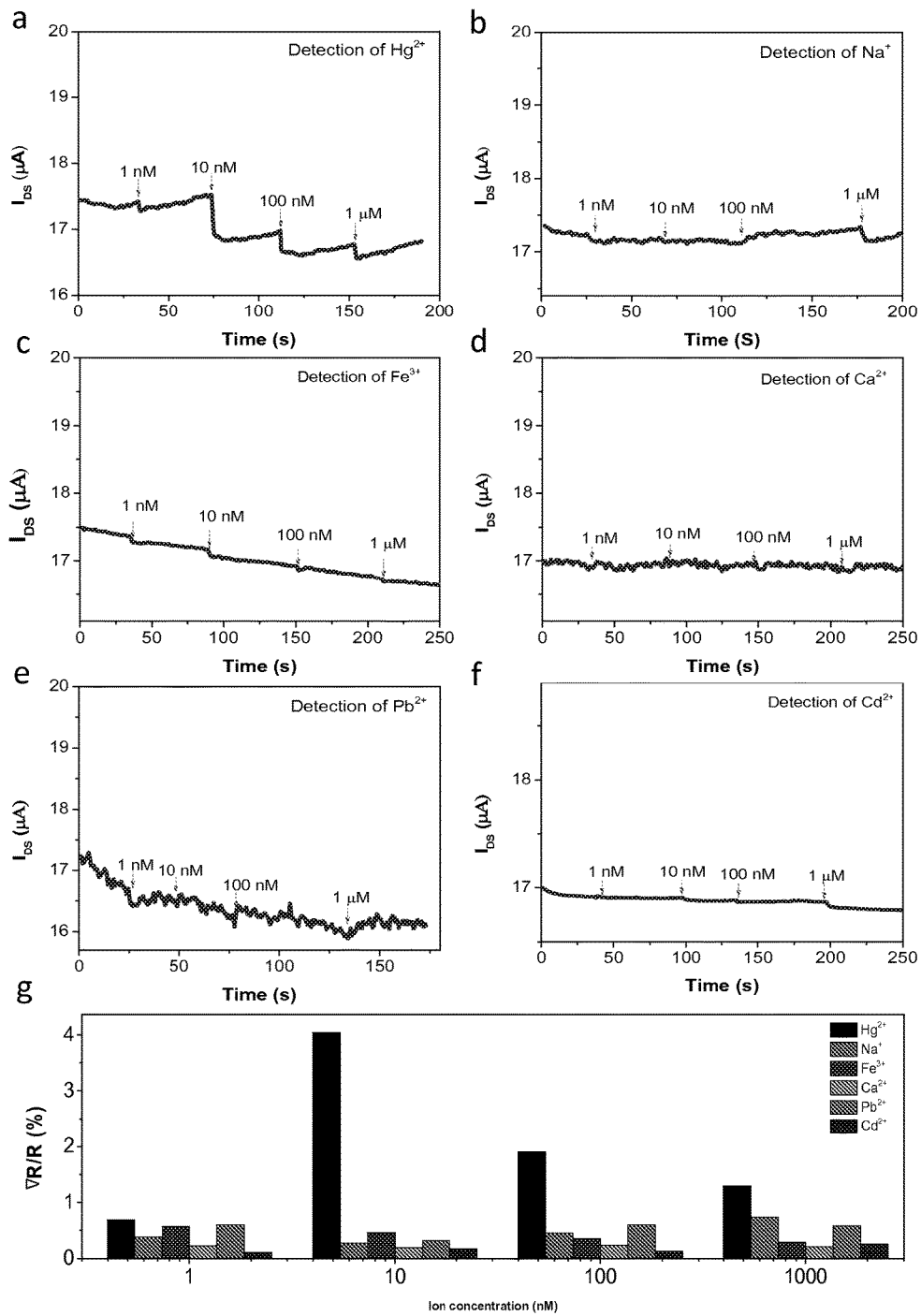
FIGS. 14A-G show the dynamic responses of the rGO/$Al_2O_3$/DNA sensor to $Hg^{2+}$ (A) and other common metal ions: (B) $Na^+$, (C) $Fe^{3+}$, (D) $Ca^{2+}$, (E) $Pb^{2-}$, and (F) $Cd^{2+}$. (G) Sensor sensitivity (relative resistance change, %) versus different metal ion concentrations. For all measurements, $V_{DS}$=0.1 V and $V_G$=0 V.

The sensing performance of rGO/$Al_2O_3$/DNA devices was investigated using a DNA-based probe for mercury ion detection, resulting in a highly selective $Hg^{2+}$ sensor. The applied $V_{DS}$ was limited to 0.1 V in order to keep the device stability for operation under aqueous conditions. Upon introduction of $Hg^{2+}$ to the rGO/$Al_2O_3$/DNA sensor, the $Hg^{2+}$-binding aptamer undergoes a conformational change, resulting in a rearrangement through thymidine (T)-$Hg^{2+}$-T coordination. During the accumulation of $Hg^{2+}$ on the devices, the increased positive charges at the sensor surface induce a stronger electrical field, which ultimately results in a decrease in the drain-source current ($I_{DS}$) in the p-type transistor. To investigate the sensitivity, the device was exposed to varying concentrations of $Hg^{2+}$ aqueous solutions. FIG. 14A illustrates the dynamic response of devices when adding selected concentrations of $Hg^{2+}$ ($10^{-9}$, $10^{-8}$, $10^{-7}$, and $10^{-6}$M). For the validation of the solution concentrations, $Hg^{2+}$ concentrations were measured using an inductively coupled plasma mass spectrometer. FIG. 14A shows that the conductance of the devices continued to decrease markedly in response to $Hg^{2+}$ with increasing concentrations. The real-time detection of $Hg^{2+}$ was possible as low as 1 nM. The real-time responses from the FET type rGO-based water sensor in response to changes in the $Hg^{2+}$ concentrations was a rapid readout (several seconds) and the detection limit was low. Those sensing data were repeated by more than 10 sensors and their similar sensing responses further confirmed the sensor repeatability and the relative standard deviation (RSD) of sensitivity at 1 nM has been calculated to be 17.20%/ To further characterize the rGO/$Al_2O_3$/DNA sensor, the sensitivity as a function of the $Hg^{2+}$ concentration was investigated. The sensitivity gradually increased from 1 nM to 1 µM of $Hg^{2+}$ concentrations with saturation observed at about 1 µM.

Figure 15:
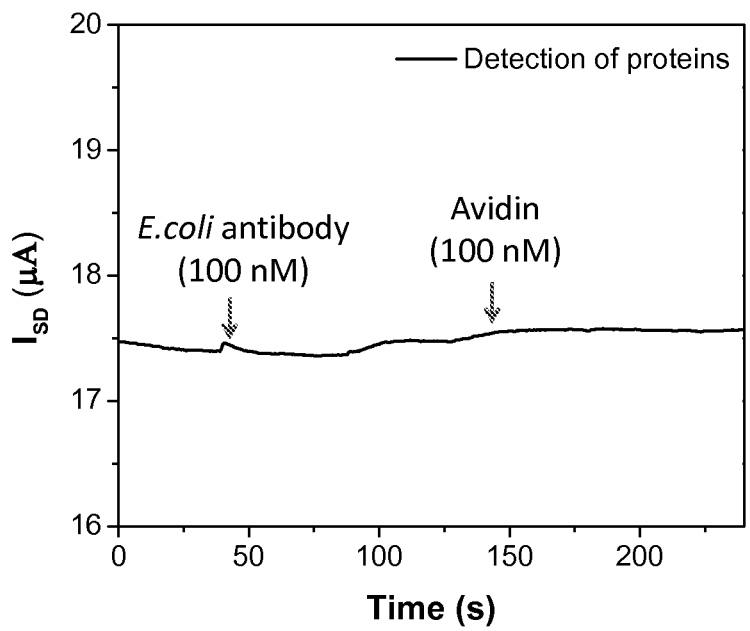
FIG. 15 shows sensing data of an rGO/$Al_2O_3$/DNA sensor for detecting proteins (E. coli antibody and avidin).
Figure 16:
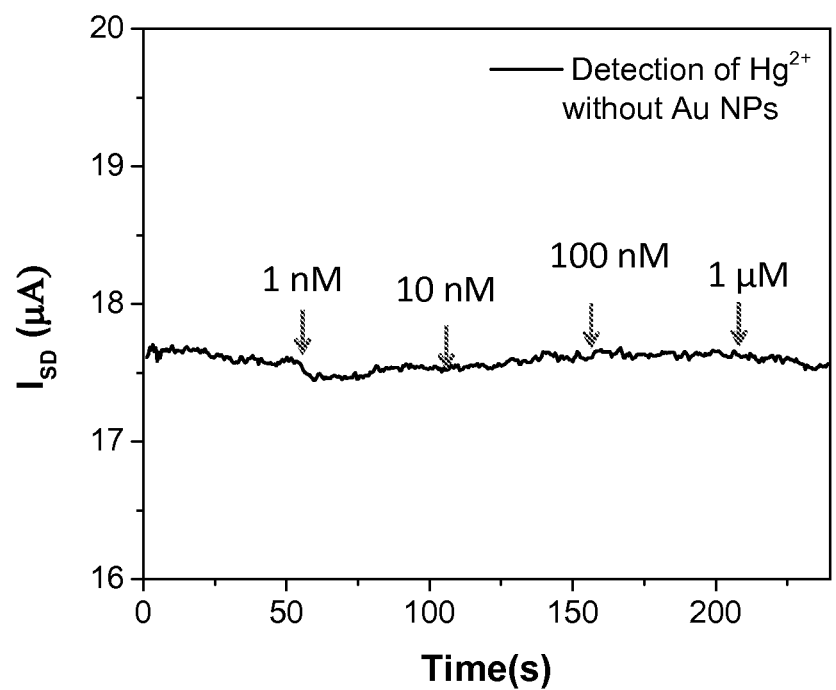
FIG. 16 shows the dynamic response of an rGO/$Al_2O_3$ sensor (without decoration of Au NPs) for detecting $Hg_±$.

To establish the sensor's specificity and reproducibility for $Hg^{2+}$ detection in the field, the response to other potential contaminants must be minimized The sensor was tested with a variety of other ions including common environmental contaminants, e.g., $Na^+$, $Fe^{3+}$, $Ca^{2-}$, $Pb^{2+}$, and $Cd^{2+}$ with the same procedure as that used for $Hg^{2+}$. The DNA probe for highly selective sensing of $Hg^{2+}$ using the formation of DNA-$Hg^{2+}$ complexes has been reported while testing against a subset of these ions. The additional ions resulted in slight decreases of $I_{DS}$ as shown in FIG. 14B-F. This response may have resulted from the electrostatic interactions between the negatively charged DNA and the positive charged ions. Furthermore, the rGO/$Al_2O_3$/DNA sensor was tested for detection of proteins (E.coli antibody and avidin), which did not show any response FIG. 15. Another control experiment was conducted using an rGO device with a 2 nm—thick $Al_2O_3$ film, but without the decoration of Au NPs. The rGO/$Al_2O_3$ device was not responsive to the $Hg^{2+}$ ions (FIG. 16). The sensor sensitivity (relative resistance change, %) as a function of the metal ion concentration (nM) shown in FIG. 14G indicates the rGO/$Al_2O_3$/DNA devices show a much higher sensitivity to each $Hg^{2+}$ concentration than that of other metal ions.

Figure 17:
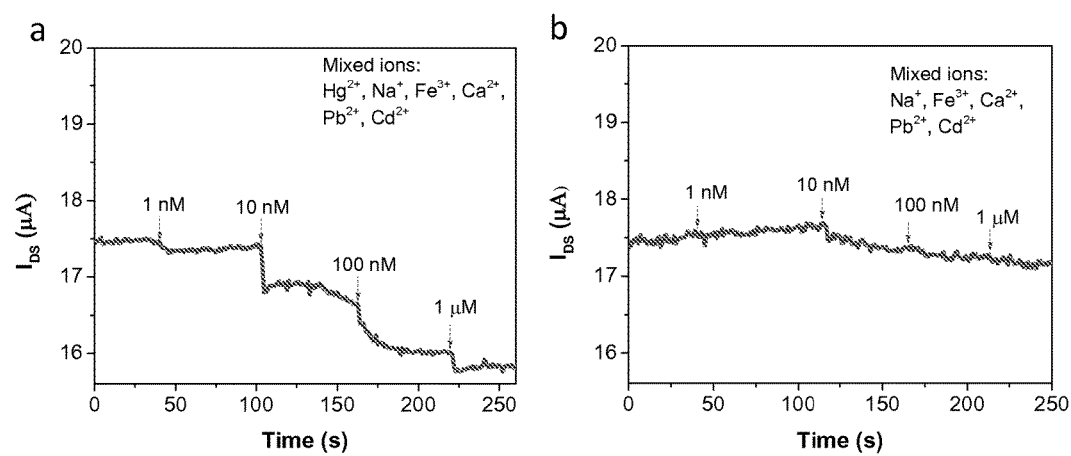
FIGS. 17A-B show the interference testing of the sensor platform. Dynamic response of the rGO/Al$_2$O$_3$/DNA FET device exposed to mixed metal ions (A) including Hg$^{2+}$ and (B) without Hg$^{2+}$.
Figure 18:
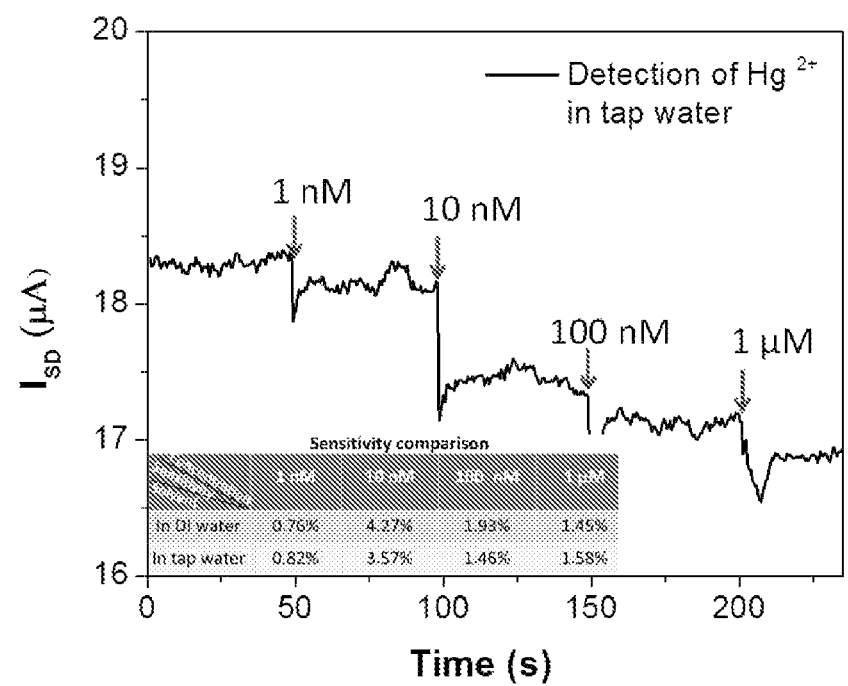
FIG. 18 shows the performance of an rGO/Al$_2$O$_3$/DNA sensor for detecting Hg2+ in tap water.

The sensor's capability was also investigated for selective detection of $Hg^{2+}$ in complex solutions. While testing with a complex sample containing multiple ionic species ($Na^+$, $Fe^{3+}$, $Cd^{2+}$, $Pb^{2+}$, and $Hg^{2+}$, the same concentration of each metal ion with $Hg^{2+}$ in the mixture solution), the sensor showed a similar trend with the detection of $Hg^{2+}$ alone, which means that sensing interference from other metal ions is negligible (FIG. 17A), as has been previously observed for the detection of $Hg^{2+}$ with carbon nanotubes.[40] Without $Hg^{2+}$, the devices showed a weak response to a complex sample at 1 nM, likely resulting from nonspecific binding between DNA and ions. Subsequent exposure of the devices to the complex sample lacking $Hg^{2+}$ resulted in a minimal sensing signal. The response of the DNA-functionalized devices to the solution with $Hg^{2+}$ is significantly higher than that to the solution without $Hg^{2+}$ due to the rearrangement of the $Hg^{2+}$-binding DNA sequence by $Hg^{2+}$. Ultimately, the high selectivity of the sensing platform for $Hg^{2+}$ demonstrates the ability for specific detection of a selective target, while the platform's capability for sensing without any other ion interference in complex solutions demonstrates its viability for specific detection in a highly complex environment. The sensors also showed good performance in real water sensing (Tap water from Milwaukee). (FIG. 18).

Example 5

Detection Limit Comparison With and Without $Al_2O_3$ Layer

Materials: GO was ordered from ACS MATERIAL, which was synthesized by using the modified Hummer's method. 2-aminoethanethiol (AET) and glutaraldehyde (GA) were purchased from Sigma-Aldrich. Tween 20 and cold water fish gelatin were ordered from Tedpella. Anti-*E. coli* O157:H7 Antibody and *E. coli* O157:H7 cells were purchased from KPL, Inc. PBS (pH 7.4, ×1) (Fisher BioReagents) was used as the solvent for anti-*E. coli* O157:H7 Antibody. All solutions were prepared with deionized (DI) water (Cellgro). Cell culture grade water was purchased from Mediatech, Inc Device fabrication: The rGO FETs were fabricated by self-assembly of GO sheets on the AET-modified Au interdigitated electrodes with both finger-width and inter-finger spacing (source and drain separation) of about 2 μm and a thickness of 50 nm. Next, the GO-deposited device was annealed in an argon flow (1 liter per minute) for 1 h at 400° C. to reduce oxygen-containing groups in order to improve the semiconducting property.

$Al_2O_3$ passivation layers were deposited on the electrode by atomic layer deposition (ALD). Trimethylaluminum (TMA) and water were the two precursors for the binary reaction at 200° C. using 10 s diffusion time and 10 s interval between the two pulses. The thickness of the $Al_2O_3$ layer was controlled precisely by the deposition cycles, with a deposition rate of 0.12 nm/cycle, which is 2 nm.

Immobilization: The prepared device was immersed into AET (1 mg/ml) solution at a concentration of 10 mM for 1 h. After thoroughly rinsed with DI water and dried under the stream of nitrogen gas, the modified device was treated by a 25% GA solution at 25° C. for 1 h. After that, the device was incubated in PBS containing anti-*E. coli* O157 (10 μg/mL) antibody at 4° C. for 12 h. At last, the device was incubated with blocking buffer (0.1% tween 20) for 2 h at room temperature and then washed with the cell culture water.

Figure 19:
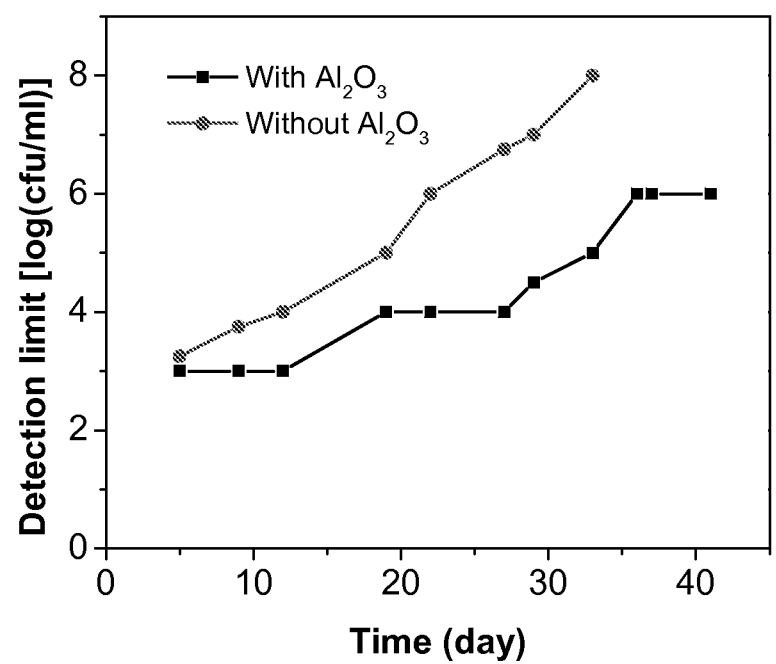
FIG. 19 shows a comparison of detection with and without an Al$_2$O$_3$ insulating layer on the rGO based field effect transistor (FET) electrodes.
Figure 20:
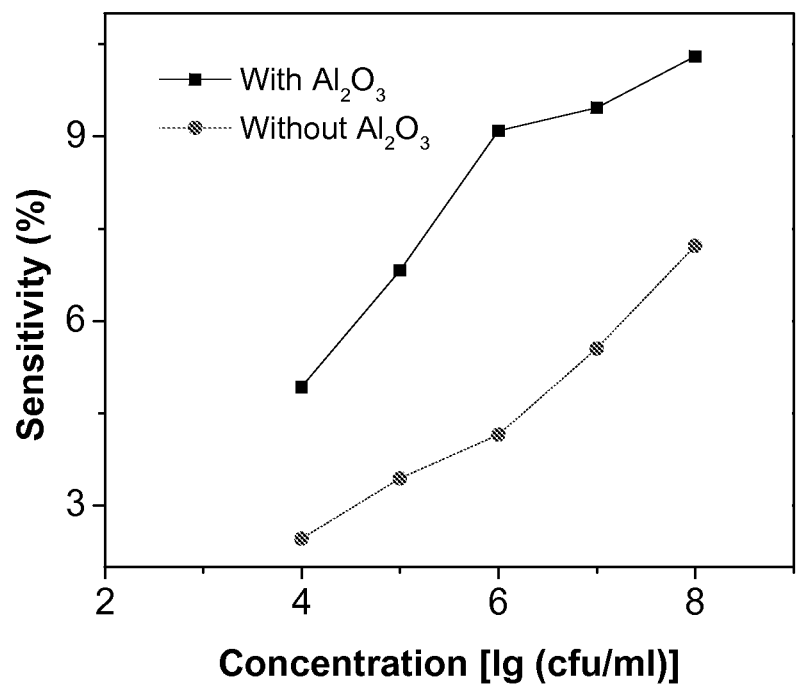
FIG. 20 shows a sensitivity comparison with and without Al$_2$O$_3$ insulating layer on the rGO based FET electrodes
Figure 21:
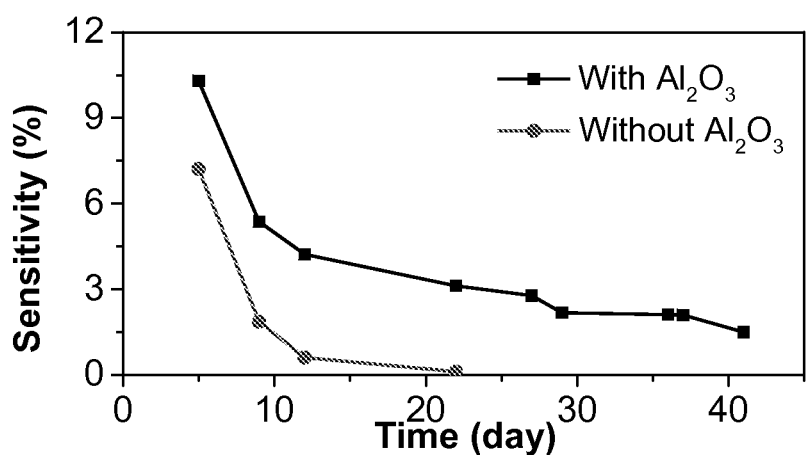
FIG. 21 shows the sensor performance decay comparison with and without Al$_2$O$_3$ insulating layer on the rGO based FET electrodes.

Results: The devices with $Al_2O_3$ insulting layers perform better than those without the $Al_2O_3$ insulating layers. The rGO FET sensor devices with $Al_2O_3$ insulating layers have lower detection limits during the 40-day test. (FIG. 19). The rGO FET sensor devices with $Al_2O_3$ insulating layers also have higher sensitivity for each concentration. (FIG. 20).

Example 6

Use of rGO/DNA/Al2O3 Sensor for Detection of $Hg^{2+}$

Figures 22, 23:
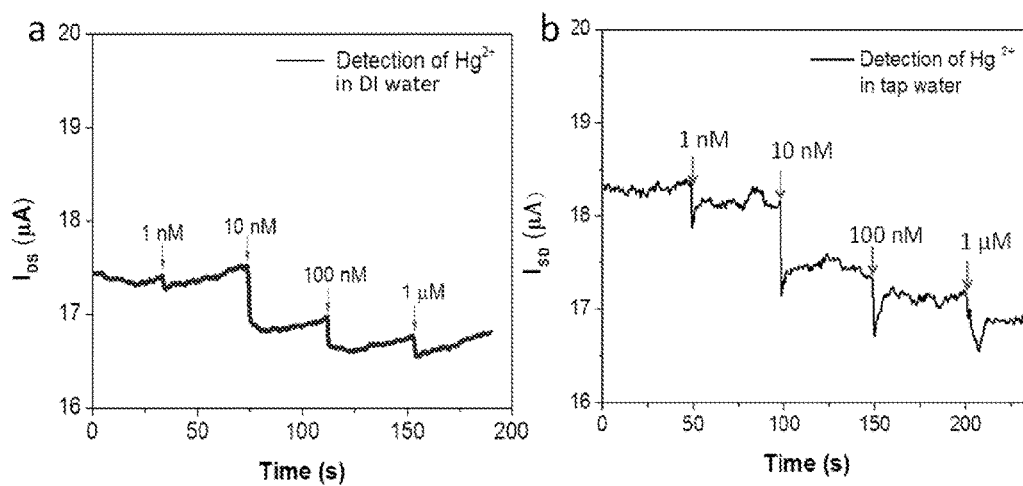
FIG. 22 shows the real-time response from the FET type rGO-based water sensor in response to changes in the Hg$^{2+}$ concentrations.
FIG. 23 shows the sensing performance of the rGO/Al$_2$O$_3$/DNA sensor in tap water compared to DI water.

To investigate the sensitivity, a device according to the present invention was exposed to varying concentrations of $Hg^{2+}$ aqueous solutions. The conductance of the devices continued to decrease markedly in response to $Hg^{2+}$ with increasing concentrations. The real-time detection of $Hg^{2+}$ was possible as low as 1 nM. The real-time response from the FET type rGO-based water sensor in response to changes in the $Hg^{2+}$ concentrations was a rapid readout (several seconds) and the detection limit was low. (FIG. 22). The sensing performance of the $rGO/Al_2O_3$/DNA sensor in tap water was comparable with that in the DI water. (FIG. 23).

Example 7

Electrical Properties of $rGO/Al_2O_3$/Au NP FET-based Sensors

Materials: GO was ordered from ACS MATERIAL and synthesized using the modified Hummer's method (Park and Ruoff 2010), and 2-aminoethanethiol (AET) was purchased from Sigma-Aldrich. All solutions were prepared with deionized (DI) water (Cellgro).

Deposition of GO on the electrodes: The rGO FETs were fabricated by self-assembly of GO sheets on the AET-modified Au interdigitated electrodes with both finger-width and inter-finger spacing (source and drain separation) of about 2 μm and a thickness of 50 nm. The process of depositing GO sheets on the electrodes using the self-assembly method has been reported in our previous publication (Chang et al. 2013 c). Next, the GO-deposited device was annealed in an argon flow (1 liter per minute) for 1 h at 400° C. to reduce oxygen-containing groups in order to improve the semiconducting property.

$Al_2O_3$ film deposition by ALD and Au NP deposition by sputtering: $Al_2O_3$ passivation layers were deposited on the electrode by atomic layer deposition (ALD). Trimethylaluminum (TMA) and water were the two precursors for the binary reaction at 200° C. using 10 s diffusion time and 10 s interval between the two pulses. The thickness of the $Al_2O_3$ layer was controlled precisely by the deposition cycles, with a deposition rate of 0.12 nm/cycle. Isolated Au nanoparticles (NPs) as scaffolds for immobilizing special probes were deposited on the $Al_2O_3$ using an RF (60 Hz) Emitech K550x Sputter coater apparatus with an Au target (99.999% purity) at an Ar pressure of 0.03 mbar.

Figure 24:
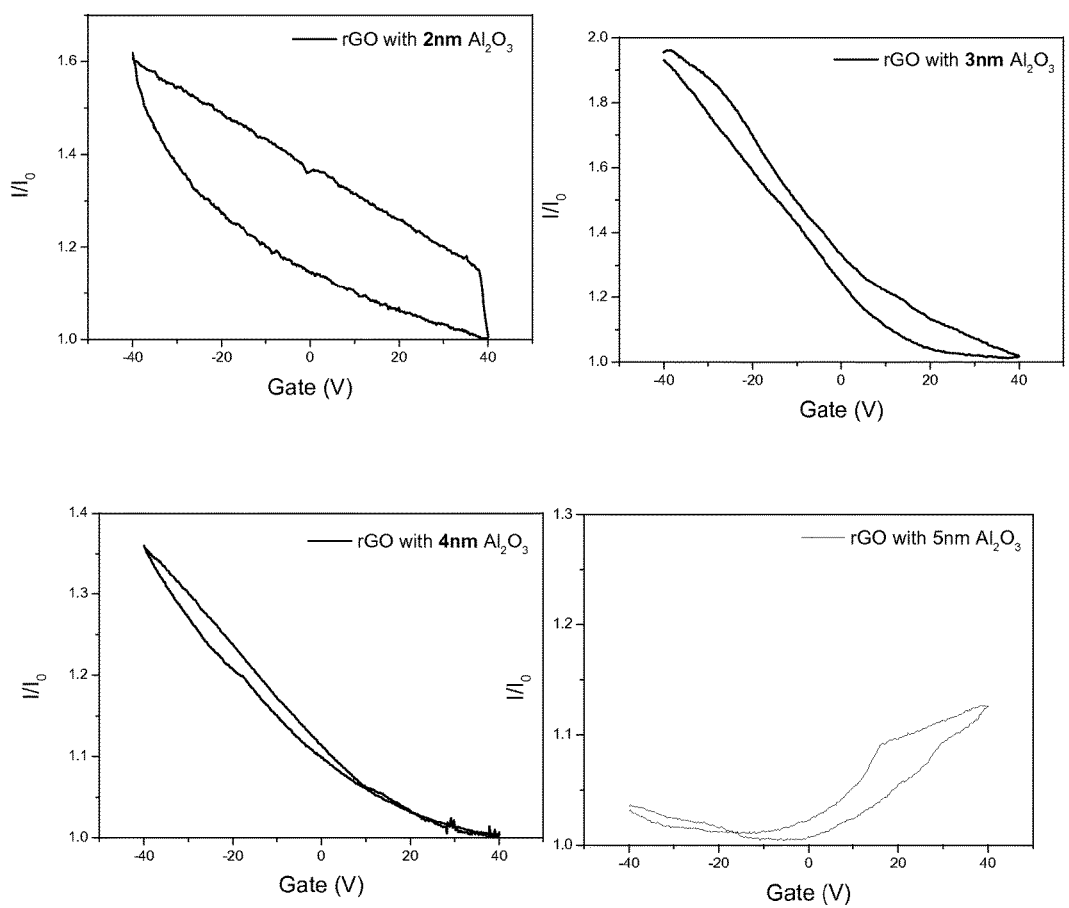
FIGS. 24A-D show the effect of varying thicknesses of the Al$_2$O$_3$ layer.

Results: To investigate the electrical properties of $rGO/Al_2O_3$/Au NP FET devices, outputs (drain-source voltage ($V_{DS}$)=0.1 V and gate-source voltage ($V_{GS}$) from −40V to 40 V) were applied into back-gated FET devices under ambient conditions at room temperature. The current on/off ratio of $rGO/Al_2O_3$/DNA FET sensors is one of important factors, which can determine the sensor sensitivity. Through investigation of effect of the thickness of $Al_2O_3$ on electrical properties of rGO, it was found that the $rGO/Al_2O_3$/DNA sensor with 3 nm thick $Al_2O_3$ coating shows the best switching performance with a current on/off current ratio of 1.9. (FIG. 24)

Various features and advantages of the invention are set forth in the following claims.

What is claimed is:

1. A field-effect transistor sensor for detecting a target in an aqueous environment comprising:
   a reduced graphene oxide layer coated with a passivation layer;
   one or more gold nanoparticles in contact with the passivation layer; and
   at least one probe bound to the one or more nanoparticles; wherein the nanoparticles are discrete nanoparticles, and wherein the passivation layer is about 1 to about 4 nanometers thick.

2. The sensor of claim 1, wherein the passivation layer is aluminum oxide.

3. The sensor of claim 1, wherein the passivation layer is about 1 to about 3 nanometers thick.

4. The sensor of claim 3, wherein the passivation layer is about 3 nanometers thick.

5. The sensor of claim 1, wherein the gold nanoparticles are distributed uniformly on the reduced graphene oxide layer.

6. The sensor of claim 1, wherein the gold nanoparticles are about 3 to about 5 nanometers in size.

7. The sensor of claim 1, wherein the gold nanoparticles are at least 5 nanometers apart.

8. The sensor claim 1, wherein more than one probe is bound to the one or more nanoparticles.

9. The sensor of claim 8, wherein the more than one probes are different.

10. The sensor of claim 1, wherein a target is a contaminant.

11. The sensor of claim 1, wherein a target is a water additive.

12. The sensor of claim 1, wherein the at least one probe detects a target selected from anions, cations, metals, viruses, bacteria, organic contaminants or a combination thereof.

13. The sensor of claim 12, wherein the bacteria are Giardia sp., Ligonella sp., or Escheria coli.

14. The sensor of claim 1, wherein the sensor is connected to a display.

15. The sensor of claim 1, wherein the at least one probe detects a target that is a metal.

16. The sensor of claim 15, wherein the metal is selected from lead, arsenic, cadmium, copper, iron, or mercury, or a combination thereof.

17. The sensor of claim 15, wherein the probe comprises thioglycolic acid (TGA) or an aptamer.

18. The sensor of claim 1, wherein the passivation layer is about 2 to about 4 nanometers thick.

19. A method for detecting a target in an aqueous sample comprising:
   a. contacting an aqueous sample with a sensor according to claim 1;
   b. applying a current to the sensor; and
   c. detecting a change in an electrical characteristic.

20. The method of claim 19, wherein the electrical characteristic is resistance.

21. The method of claim 19, wherein more than one target is detected in the sample using a single sensor with more than one probe.

22. The method of claim 19, wherein the aqueous sample is from one selected from a group of a water distribution system and a wastewater treatment process.

23. The method of claim 19, wherein the change in resistance is detected continuously.

24. The method of claim 19, wherein the change in resistance is detected periodically by the sensor.

25. The method of claim 19, further comprising transmitting the change in resistance to a display.

* * * * *